(12) United States Patent
Nakamura et al.

(10) Patent No.: US 6,398,721 B1
(45) Date of Patent: Jun. 4, 2002

(54) SURGICAL MICROSCOPE APPARATUS

(75) Inventors: Motokazu Nakamura, Hino; Masaaki Ueda, Sagamihara; Toru Shinmura; Keiji Shioda, both of Hachioji; Kyo Imagawa, Ome; Nobuaki Akui, Hino; Shigeyasu Kishioka, Kokubunji; Koji Yasunaga, Hino; Junichi Nozawa; Takashi Fukaya, both of Sagamihara; Toshiya Sugai, Tokyo; Koji Shimomura; Hitoshi Karasawa, both of Hachioji; Kazutaka Nakatsuchi; Takeaki Nakamura, both of Hino, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/506,059

(22) Filed: Feb. 17, 2000

(51) Int. Cl.[7] .............................. A61B 1/00; G02B 21/06
(52) U.S. Cl. .................. 600/102; 600/160; 600/178; 359/385
(58) Field of Search ................................. 600/101, 102, 600/160, 166, 178; 359/368, 385, 388

(56) References Cited

U.S. PATENT DOCUMENTS 4,614,410 A * 9/1986 Ikenaga et al. ............ 359/368
4,621,531 A * 11/1986 Nakamura et al. ......... 359/368
5,095,887 A * 3/1992 Leon et al. ................ 359/375
5,601,549 A   2/1997 Miyagi
6,081,371 A * 6/2000 Shioda et al. ............. 359/369
6,106,456 A * 8/2000 Storz ......................... 600/102

FOREIGN PATENT DOCUMENTS

| JP | 62-166310 | 7/1987 |
| JP | 4-83223 | 7/1992 |
| JP | 7-261094 | 10/1995 |
| JP | 8-131455 | 5/1996 |
| JP | 10-333047 | 12/1998 |

* cited by examiner

*Primary Examiner*—John P. Leubecker
(74) *Attorney, Agent, or Firm*—Frishauf, Holtz, Goodman, Langer & Chick, P.C.

(57) ABSTRACT

A surgical microscope apparatus incorporating a frame portion placed on a floor, a microscope body for stereoscopically observing a portion to be operated, an arm portion supported by the frame portion and arranged to suspend the microscope body, and an endoscope for observing a blind spot for a stereoscopic observation field of view. The frame portion has a light source unit for generating light for illuminating a portion observed with the endoscope and a camera control unit for processing an observed image of an observed portion obtained by the endoscope. A light guide fiber extending from the light source unit to the microscope body and capable of supplying light to the endoscope, and a camera cable for transmitting the image observed with the endoscope to the camera control unit extend in the arm portion. The microscope body is provided with an end of the light guide fiber for connecting the endoscope and a camera head connected to the camera cable.

25 Claims, 15 Drawing Sheets

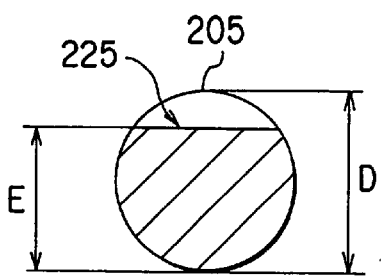
FIG. 26
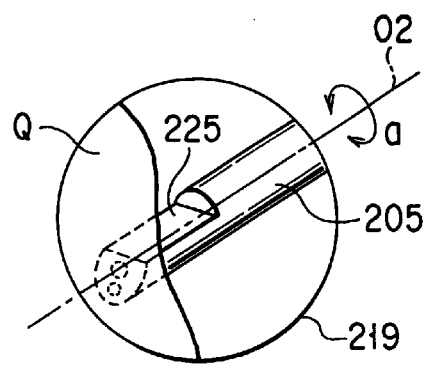
FIG. 27
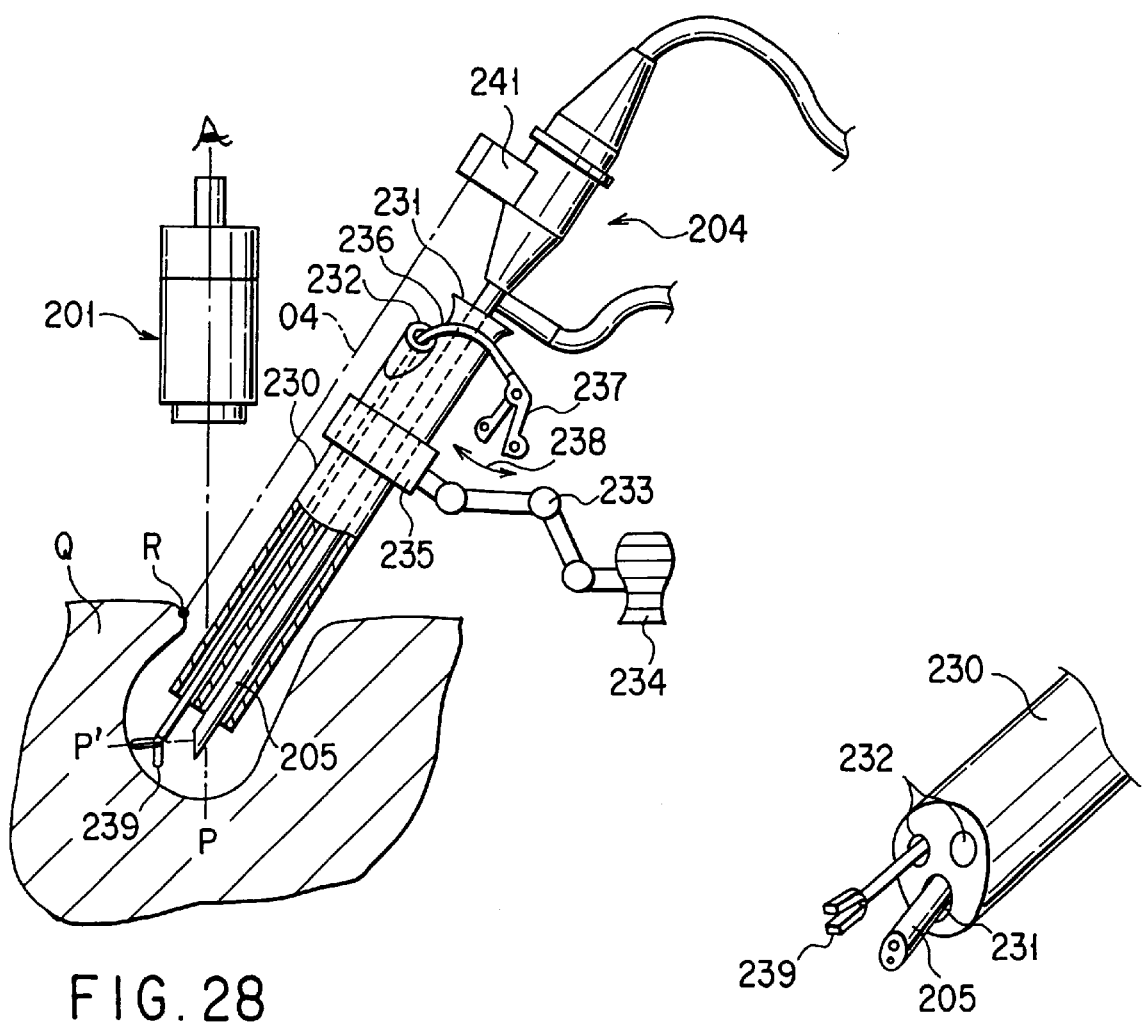
FIG. 28
FIG. 29

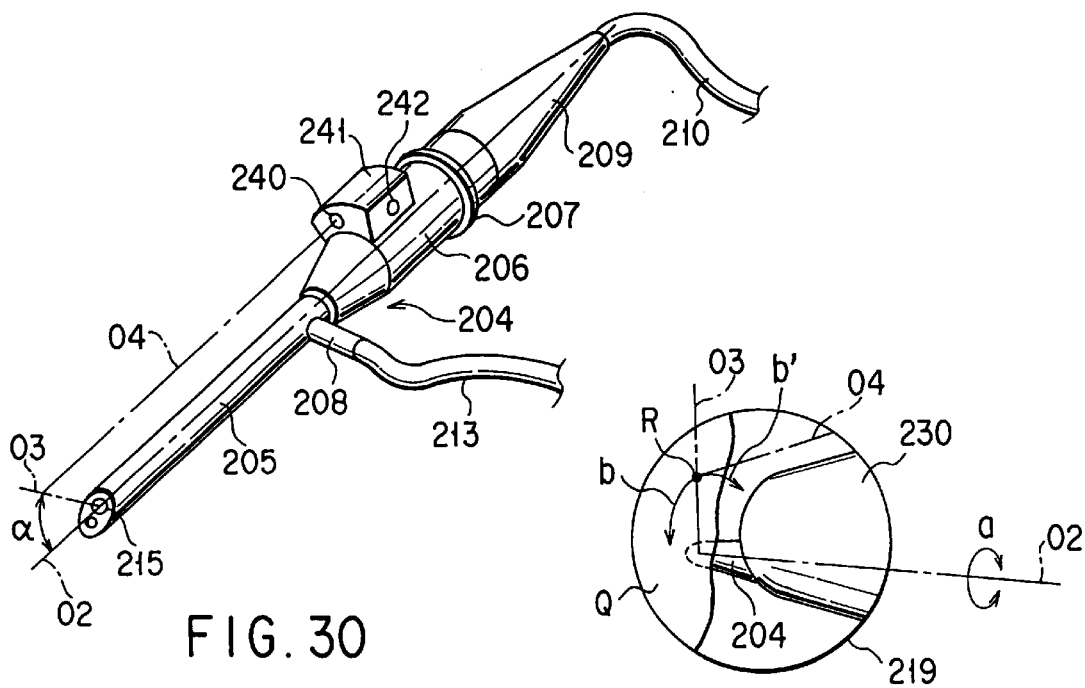
FIG. 30
FIG. 31
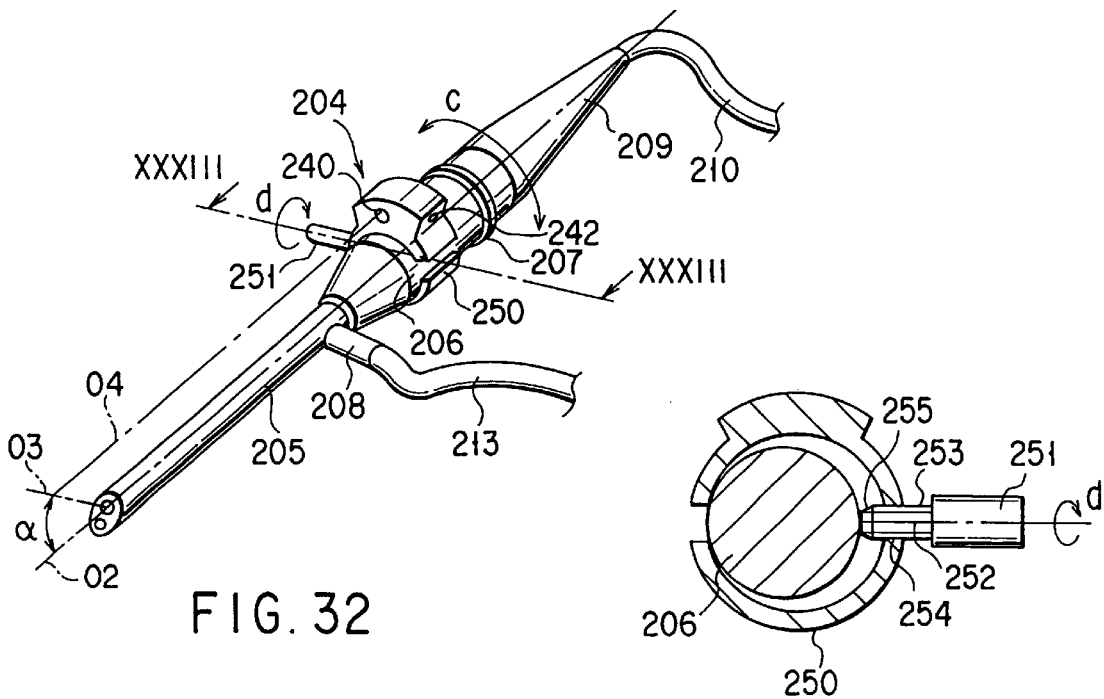
FIG. 32
FIG. 33

SURGICAL MICROSCOPE APPARATUS

CROSS-REFERENCE TO RELATED APPLICATIONS

This application is based upon and claims the benefit of priority from the prior Japanese Patent Applications No. 11-041806, filed Feb. 19, 1999; No. 11-089399, filed Mar. 30, 1999; and No. 2000-018865, filed Jan. 27, 2000, the entire contents of which are incorporated herein by reference.

BACKGROUND OF THE INVENTION

The present invention relates to a microscope apparatus for performing surgery also using an endoscope.

In recent years, microsurgery which is surgery of a small affected part has been developed and widely used. Therefore, microsurgery has frequently been performed in a variety of medical fields, such as the neurosurgery, otolaryngology and ophthalmology. The microsurgery is performed while observation using a surgery microscope is being performed. In particular, non-invasive surgery has been performed to permit quick rehabilitation after the surgery. In particular, attention is being paid to surgery also using a so-called endoscope for observing a portion (a dead zone) which is invisible during observation using the conventional microscope for surgery.

When a portion to be operated is observed with an endoscope in the neurosurgery, the direction of observation with the endoscope must easily be recognized by an operator.

Moreover, low invasion is required to satisfactorily prevent pressing of the portion in the vicinity of the operated portion when the endoscope is operated. Therefore, when the endoscope is operated while observation is being performed with the microscope for surgery, the operation must be performed such that the position into which the endoscope has been inserted is always confirmed.

There are systems of a type with which an image observed with an endoscope is also displayed in a field of view of a surgical microscope. The systems are disclosed in Jpn. Pat. Appln. KOKAI Publication No. 10-333047, Jpn. Pat. Appln. KOKAI Publication No. 7-261094, Jpn. Pat. Appln. KOKAI Publication No. 62-166310, U.S. Pat. No. 5,601,549 and Jpn. Pat. Appln. KOKAI Publication No. 8-131455. The surgical microscope disclosed in Jpn. Pat. Appln. KOKAI Publication No. 10-333047 has a structure that an image observed with an endoscope is simultaneously displayed in an upper region of an image observed with a microscope.

The endoscope for use in the conventional surgical microscope is arranged to illuminate a portion observed with the endoscope or a portion taken by a solid-state image sensing device. To perform illumination, a special light source unit disposed individually supplies light to the endoscope through a light guide fiber.

A surgical microscope for use in an ophthalmic surgery is known which has a structure as disclosed in Jpn. UM. Appln. KOKAI Publication No. 4-83223. That is, a light source provided in a frame for a surgical microscope supplies light to a probe for illuminating the inside portion of the eye so that the inside portion of the eye is illuminated.

The conventional system disclosed in Jpn. Pat. Appln. KOKAI Publication No. 10-333047, Jpn. Pat. Appln. KOKAI Publication No. 7-261094 and Jpn. Pat. Appln. KOKAI Publication No. 62-166310 must have the special light source for the endoscope. Therefore, the cost of the endoscope system cannot be reduced. Moreover, a carrier, such as a cart, is required to mount the light source in the operation room. Thus, the usable space in the operation room is undesirably reduced. Since the light source unit cannot be sterilized, the light source unit must be disposed sufficiently apart from the portion to be operated. Hence it follows that a long light guide fiber for connecting the endoscope and the light source to each other is required. Moreover, the deadweight of the light guide fiber and insufficient flexibility of the same inhibit a smooth operation using the endoscope. As a result, there arises a problem in that the endoscope cannot smoothly be moved during the operation.

The apparatus disclosed in U.S. Pat. No. 5,601,549 is arranged to adjust a direction of observation using a hard scope. Thus, undesirable introduction of the distal end of the hard scope into the shadow of an organization, such as the blood vessel or the nerve, is prevented. At this time, the direction of the diagonal observation in the observation field of view of the microscope cannot easily be detected. Thus, there arises a problem in that the orientation of the observation, such as the direction of observation with the hard scope with respect to the observation field of view of the microscope, cannot be recognized.

The invention disclosed in Jpn. Pat. Appln. KOKAI Publication No. 8-131455 incorporates a hard scope integrally joined to a surgical microscope body. Moreover, a focal-plane plate is provided which has an index (an arrow) formed at an intermediate image forming point of the microscope by stamping. The hard scope and the focal-plane plate are connected to each other through gears, the reduction ratio of which is 1:1. Thus, the focal-plane plate can be rotated to correspond to the rotation with respect to the observation optical axis for changing the diagonal observation of the hard scope. As a result, the direction of observation with the hard scope with respect to the observation field view of the microscope can be detected. However, selection of a variety of hard scopes is inhibited which are different in the size and the oblique observation angles to correspond to the size of a cut portion of the operated portion and a required direction of observation with respect to the direction in which the hard scope is inserted. What is worse, insertion of the hard scope from an arbitrary direction into the portion to be operated in the observation field of view of the microscope is not permitted.

The surgical microscope disclosed in Jpn. UM. Appln. KOKAI Publication No. 4-83223 has the structure that the light source for the surgical microscope supplies light to the probe for the inside portion of the eye. Therefore, any special light source is not required. Light for the surgical microscope and light for the probe for the inside portion of the eye are supplied from one light source by switching light from the light source lamp. Therefore, the surgical microscope and the probe for the inside portion of the eye cannot simultaneously be illuminated. As a result, required observation cannot be performed.

BRIEF SUMMARY OF THE INVENTION

In view of the foregoing, an object of the present invention is to provide an apparatus by improving a conventional surgical microscope so as to enhance the surgery efficiency.

Specifically, an object of the present invention is to provide a surgical microscope apparatus which is capable of eliminating complex routing of a long cable of an auxiliary observation unit to perform microsurgery which also uses the auxiliary observation unit.

Another object of the present invention is to provide a surgical microscope with which sterilization in the vicinity of the microscope can reliably be realized when the auxiliary observation unit is used in the vicinity of the microscope.

Another object of the present invention is to provide a low-cost system which enables simultaneous illumination and observation of both of a surgical microscope and an endoscope to be performed when surgery also using the endoscope is performed to improve the operability of the endoscope and provides a sufficiently large space for an operator and satisfactory large spatial margin in the operation room.

Another object of the present invention is to provide a hard scope to be inserted into the body cavity to enable a surgeon to observe an object in the cavity through a surgical microscope, in a predetermined angular direction in a plane perpendicular to a line along which the hard scope is inserted, and to understand easily the direction of observation in the observation field of surgical microscope.

To achieve the foregoing objects, according to one aspect of the present invention, there is provided a surgical microscope apparatus comprising: a frame portion placed on a floor; a surgical microscope body incorporating a stereomicroscope optical system for stereoscopically observing a portion to be operated and an outer surface; and an arm portion supported by the frame portion to suspend the microscope body at a position apart from the frame portion. The microscope apparatus incorporates an endoscope for observing a blind spot of an observation field of view of the stereomicroscope optical system; a light source unit provided in the frame portion and emitting light for illuminating a portion which is observed by the endoscope; and light supply means having an end which can optically be connected to the endoscope to be capable of supplying light from the light source unit to the endoscope; an image control unit provided in the frame portion and arranged to process an observed image of an observed portion obtained by the endoscope; image transmission means having an end for interfacing the endoscope with the image control unit and capable of transmitting the image observed by the endoscope to the image control unit; and a connecting portion of the endoscope provided on the outer surface of the microscope body and incorporating ends of the light supply means and the image transmission means.

The surgical microscope incorporates the surgical microscope body provided with the connecting portion for the endoscope for sub-observing the blind spot for the surgical microscope. Therefore, distance for which a cable of the endoscope is routed can be shortened. Thus, the operation is not obstructed by the cable. As a result, a surgery efficiency can be improved.

It is preferable that a holding portion for detachably holding the endoscope in the vicinity of the microscope body is provided. In the foregoing case, removal of the endoscope from the holding portion permits immediate use of the endoscope. After the operation using the endoscope has been completed, the endoscope is joined to the holding portion. Thus, the endoscope can quickly be put back, causing the operation to smoothly be performed. It is preferable that the holding portion is provided for one casing together with the connecting portion.

It is advantageous that the surgical microscope apparatus further comprising: a sterilizing drape for covering the surgical microscope body to realize a sterilized state in the internal body portion, wherein the holding portion incorporates a holder having a joining portion arranged to be joined to the surgical microscope body from outside of the sterilizing drape and an accommodating portion for accommodating the endoscope, and the joining portion and the accommodating portion of the holder are spatially separated from each other. In the foregoing case, the sterilizing drape is not ripped when the observing means is joined or removed. If the joining portion rips the sterilizing drape, the sterilization of the auxiliary observation means can always be maintained because the joining portion and the accommodating portion are spatially separated from each other.

An ultrasonic probe may be employed as a substitute for the endoscope or the same may be employed together with the endoscope to observe the blind spot of the observation field of view of the stereomicroscope optical system.

In the foregoing case, the surgical microscope apparatus further comprises: a drive unit provided for the microscope body and arranged to produce a drive control signal for an ultrasonic oscillator provided for the ultrasonic probe; a relay portion for relaying an ultrasonic signal transmitted from a portion observed by the ultrasonic probe; a drive signal transmission portion for transmitting (interfacing) the drive signal to the ultrasonic probe; an ultrasonic signal transmission passage for transmitting the ultrasonic signal from the ultrasonic probe to the relay portion; and an ultrasonic probe connecting portion provided for the outer surface of the microscope body and capable of connecting the drive signal transmitting portion and the drive unit to each other.

According to another aspect of the present invention, there is provided a surgical microscope apparatus comprising: a frame portion disposed on a floor; a stereomicroscope optical system for stereoscopically observing a portion to be operated; a surgical microscope body having an outer surface; an arm portion supported by the frame portion and structured to suspend the microscope body at a position apart from the frame portion; an auxiliary observation unit for observing a blind spot of an observation field of view of the stereomicroscope optical system; an operating/control unit provided for the frame portion and arranged to operate the auxiliary observation unit; cable means extended from the operating/control unit through the arm portion and having an end disposed in the microscope body; a connecting portion for forming an interface between the auxiliary observation unit and the operating/control unit; a holding portion joined to the microscope body and detachably holding the auxiliary observation unit; a holding casing for integrally holding the connecting portion and the holding portion; and moving means provided for the holding casing and arranged to move either of the connecting portion or the holding portion with respect to the microscope body.

It is preferable that the microscope body incorporates a housing, the moving means has a hollow shaft portion provided for the holding casing and arranged to penetrate the housing and the holding casing is, by the shaft portion, rotatably supported with respect to the housing. In the foregoing case, the auxiliary observation unit can be disposed at a position at which an operator can easily handle the auxiliary observation unit.

Alternatively, the holding casing may have a joining portion detachable with respect to the microscope body. In the foregoing case, it is advantageous that the microscope body has a housing, either of the housing or the joining portion has a dovetail groove, and the other element, which is the housing or the joining portion, has a dovetail which slidably engages to the dovetail groove.

When the auxiliary observation unit is an endoscope, it is preferable that the surgical microscope apparatus incorporates another light supply means for supplying light from the light source unit to the portion to be operated; and light branching means for branching the light supply means capable of supplying light to the endoscope from the other light supply means.

In the foregoing case, simultaneous illumination to both of the surgical microscope and the endoscope is permitted when an operation also using the endoscope is performed. That is, field of views can simultaneously be observed by both of the surgical microscope and the endoscope. Since light can be supplied from a common light source unit to the surgical microscope and the endoscope, a special light source unit for the endoscope is not required. As a result, the structure can be simplified and, therefore, a low-cost apparatus can be provided. Moreover, a cart or the like for mounting the light source unit in the operation room is not required. Hence it follows that a wide space can be provided in the operation room. Since the light supply means required to only connect the endoscope and the microscope to each other can be shortened, deterioration of the operability of the endoscope owing to the deadweight and unsatisfactory flexibility of the light supply means can be prevented. Moreover, the operation of the operator is not obstructed and a sufficiently large working space can be provided.

In the foregoing case, the light branching means may comprise light passage splitting means composed of a group including a half mirror, a beam splitter and a split light guide fiber; or a light passage reflecting means composed of a group including a prism and a mirror.

It is preferable that the endoscope incorporates an elongated hard insertion portion having an axial line and a distal end which is inserted into the body along the axial line; an objective optical system provided for the distal end and having an optical axis which extends to make a predetermined angle with respect to the axial line; and identifying means provided for the distal end and indicating a direction in which the optical axis of the objective optical system extends, wherein the identifying means can stereoscopically be observed through the stereo-microscope optical system.

In a case of the foregoing surgical microscope, the operator attempts to use both of enlargement observation of a portion to be operated and observation of a blind spot portion for the observation with the microscope by using the hard scope, which enables the correlation of the position of observation performed by using the hard scope with respect to the field of view for the microscope to easily be recognized even during the observation using the microscope. Therefore, the objective lens of the hard scope can easily be moved to a desired position in the blind spot portion for the observation using the microscope. Moreover, any expensive apparatus is not required to realize a similar effect if the conventional hard scope is slightly changed or additional parts are added to the same.

The identifying means may be formed by at least one index provided for the outer surface of the distal end, an outer shape provided for the distal end and either of a portion to be operated and the endoscope joined to the endoscope.

Alternatively, the identifying means may have a projecting unit for projecting an index to at least either of the portion to be operated or the outer surface of the endoscope. The projecting unit may have a laser diode. The projecting unit may be made detachable with respect to the endoscope.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 26 is a cross sectional view taken along the line XXVI—XXVI shown in FIG. 25B;

FIG. 27 shows an image observed with the hard scope shown in FIG. 25A in an observation field of view of the surgical microscope;

FIG. 28 is a diagram showing a system incorporating the hard scope according to a seventeenth embodiment;

FIG. 29 is a perspective view showing the distal end of a sheath which is used together with the hard scope shown in FIG. 28;

FIG. 30 is a perspective view showing the hard scope shown in FIG. 28;

FIG. 31 is a diagram showing an image observed with the hard scope shown in FIG. 28 in an observation field of view of the surgical microscope;

FIG. 32 is a perspective view showing a hard scope according to an eighteen embodiment;

FIG. 33 is a cross sectional view taken along the line XXXIII—XXXIII shown in FIG. 32;

DETAILED DESCRIPTION OF THE INVENTION

[First Embodiment]

Figure 1:
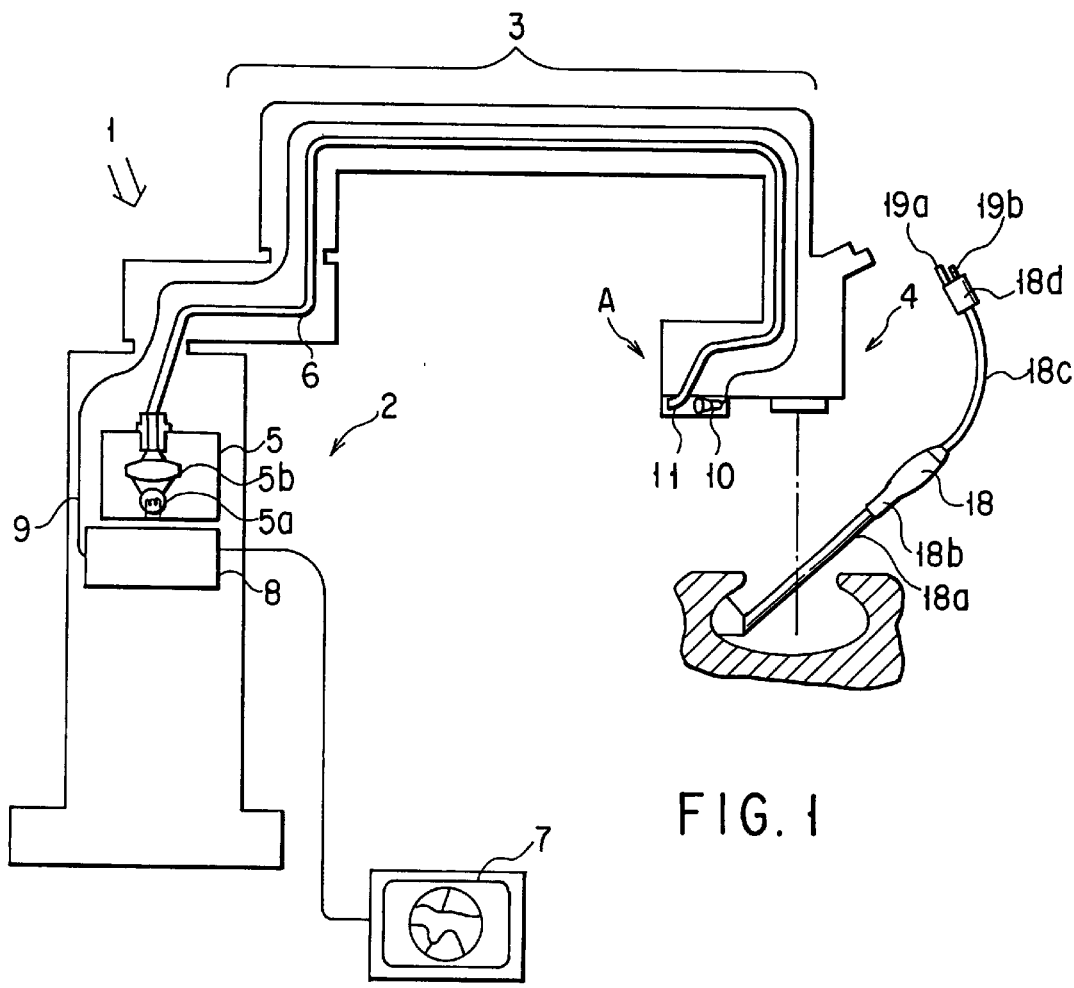
FIG. 1 is a diagram showing the schematic structure of a surgical microscope apparatus according to a first embodiment of the present invention.
Figure 2:
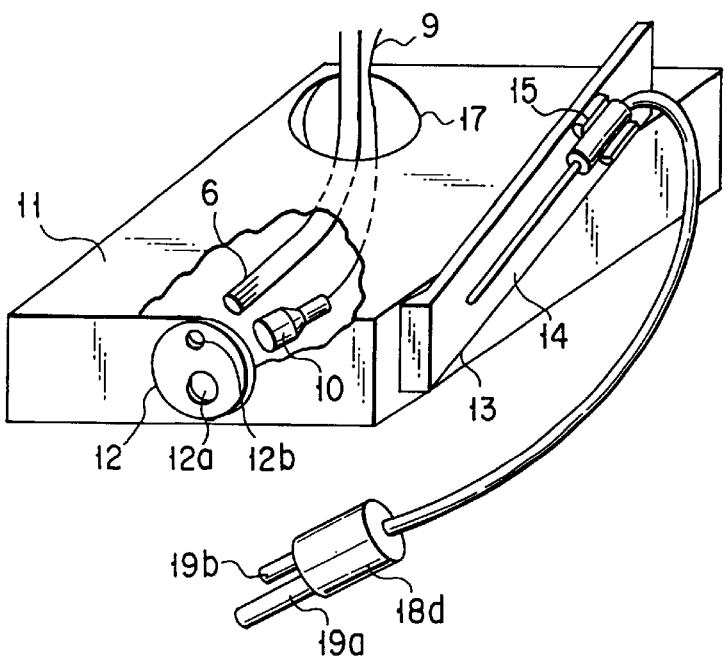
FIG. 2 is a schematic view showing a connecting/holding unit for an endoscope for use in the microscope apparatus shown in FIG. 1.
Figure 3:
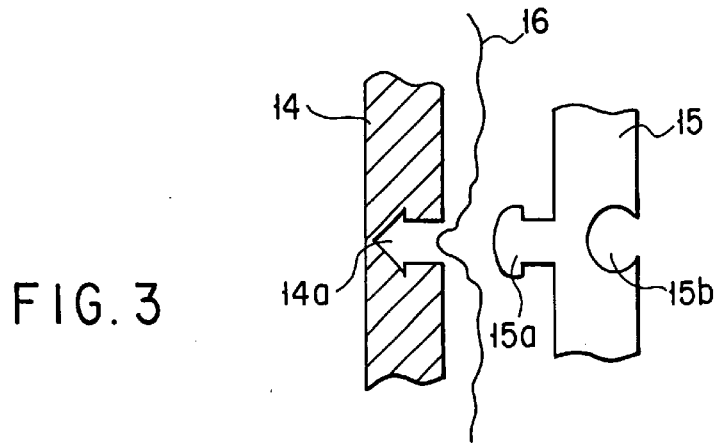
FIG. 3 is a diagram showing a state where a holding member is joined to the connecting/holding unit for the endoscope shown in FIG. 2.

Referring to FIGS. 1 to 3, a first embodiment of the present invention will now be described.

A surgical microscope apparatus 1 according to this embodiment incorporate a frame portion 2 disposed on a floor; an arm portion 3 connected to the frame portion 2; and a microscope body 4 supported by the arm portion 3. A portion to be operated is enlarged and observed by the microscope body 4. The microscope body 4 is supported by the arm portion 3 such that three-dimensional movement and inclination in a space of the microscope body 4 are permitted. A light source unit 5 is disposed in a support column of the frame portion 2. The light source unit 5 incorporates a lamp 5a and a converging lens 5b to direct light on a connected flexible light guide fiber 6. The light guide fiber 6 is allowed to pass through the frame portion 2 and the arm portion 3 to be guided to the microscope body 4.

A camera control unit 8 for displaying, on a monitor 7, an image observed by an endoscope to be described later is disposed in the support column of the frame portion 2. A camera cable 9 is connected to the camera control unit 8 so as to be routed in the frame portion 2 and the arm portion 3 to be guided to the microscope body 4. A camera head 10 accommodating which is usually smaller than the outer diameter of the endoscope to be described later. When the endoscope is pushed inwards, the C-shape accommodating portion 15b is elastically deformed in a direction in which the diameter of the C-shape accommodating portion 15b is enlarged. Then, the diameter is restored to the original diameter. Thus, the C-shape accommodating portion 15b has a function for holding the endoscope. The C-shape accommodating portion 15b is made of material which can be sterilized.

Note that the surgical microscope apparatus 1 and the endoscope connecting/holding unit 11 are covered with a sterilizing drape 16 for sterilizing the surgical microscope apparatus 1 and the endoscope connecting/holding unit 11. The projection 15a is structured such that when the recess 14a of the frame 14 and the projection 15a of the holder 15 are engaged to each other, the projection 15a is pushed into the recess 14a along with the sterilizing drape 16. The magnitude required to push and draw the recess 14a and the projection 15a is made to be larger than that required between the C-shape accommodating portion 15b and the endoscope.

Referring to FIG. 2 again, the camera head 10 is disposed at the rear of the observing-system connecting portion 12a of the endoscope connecting portion 12. An end surface of the light guide fiber 6 is disposed at a CCD is disposed at an end of the camera cable 9. An endoscope connecting/holding unit 11 to connect and hold the endoscope, which serves as an auxiliary observation means and will be described later, is disposed below the microscope body 4.

FIG. 2 shows the appearance of the endoscope connecting/holding unit 11 when the endoscope connecting/holding unit 11 is viewed from the direction A shown in FIG. 1. The endoscope connecting/holding unit 11 is provided with an endoscope connecting portion 12 serving as a connecting portion and an endoscope holding portion 13 serving as a holding portion.

The endoscope connecting portion 12 incorporates an observing-system connecting portion 12a and an illuminating-system connecting portion 12b. The endoscope holding portion 13 incorporates a frame 14 formed upwards on the right-hand side of the endoscope connecting/holding unit 11 when it is viewed in FIG. 2 and a holder 15 connected to the frame 14.

As shown in FIG. 3, the frame 14 and the holder 15 are secured when a projection 15a which is a joining portion of the holder 15 is introduced into a recess 14a of the frame 14. The holder 15 incorporates a C-shape accommodating portion 15b serving as a portion for accommodating auxiliary observation means. The C-shape accommodating portion 15b has an inner diameter the rear of the illuminating-system connecting portion 12b. The camera cable 9 of the camera head 10 and the light guide fiber 6 are extended to the outside of the endoscope connecting/holding unit 11 through an opening 17. Thus, the camera cable 9 and the light guide fiber 6 are introduced into the microscope body 4 through an opening (not shown) formed in a lower portion of the microscope body 4 of the surgical microscope apparatus 1.

FIG. 1 furthermore shows the endoscope given reference numeral 18 and arranged to observe a blind spot in an observation field of view of the microscope body 4 of the surgical microscope apparatus 1. The endoscope 18 incorporates an insertion portion 18a and a body 18b. An endoscope cable 18c extends from the body 18b, the endoscope cable 18c having an end provided with a connector 18d.

The connector 18d of the endoscope 18 incorporates an observing-system connector 19a and an illuminating-system connector 19b. An observation optical system including an image guide fiber and an objective lens and an illumination optical system including a light guide fiber (not shown) are connected to the foregoing connector 19a and 19b. The foregoing optical systems are optically connected to the distal end of the insertion portion 18a of the endoscope 18.

The connector 18d has a size and a shape with which connection of the connector 18d with the endoscope connecting portion 12 of the endoscope connecting/holding unit 11 is permitted. The sterilizing drape 16 has perforations for permitting insertion of the connector 18d in a portion corresponding to the endoscope connecting portion 12.

(Operation)

When the surgical microscope apparatus 1 according to the first embodiment is operated, the surgical microscope apparatus 1 and the endoscope connecting/holding unit 11 are covered with the sterilizing drape 16 as a first step. Then, as shown in FIG. 3, the projection 15a of the holder 15, which has been sterilized, is pushed into the recess 14a of the frame 14 from a position above the sterilizing drape 16. Then, the sterilizing drape 16 are cut along the perforations to connect the connector 18d of the endoscope 18 to the endoscope connecting portion 12.

It leads to a fact that light is supplied to the endoscope 18 through the light guide fiber 6, as shown in FIG. 2. Thus, an observed image obtained by an observation optical system of the endoscope 18 is taken by the camera head 10. The taken image is converted into an electric signal and transmitted by the cable 9 so as to be displayed on a monitor 7 by the camera control unit shown in FIG. 1.

When the endoscope 18 is not operated, the endoscope 18 is pushed into the C-shape accommodating portion 15b of the holder 15 shown in FIG. 3. At this time, the C-shape accommodating portion 15b is elastically deformed such that the C-shape accommodating portion 15b is restored to the original size in a state where the endoscope 18 is accommodated. Thus, the endoscope 18 is held. When the endoscope 18 is again used, an inverse process is performed.

Although this embodiment is structured such that the endoscope holding portion 13 is disposed in the right-hand portion of the drawing, the endoscope holding portion 13 may be disposed in the left-hand portion. The endoscope is not limited to the fiber scope which has the observation system incorporating optical fiber. The endoscope may be a video scope accommodating a CCD. In the latter case, the connector of the observation system comprises an electric contact.

This embodiment is structured such that the connector 18d of the endoscope 18 is connected to the endoscope connecting/holding unit 11 disposed below the microscope body 4 of the surgical microscope apparatus 1. Therefore, the endoscope cable 18c can be shortened as much as possible, thereby to prevent the endoscope cable 18c from obstructing the operation of an operator. Since the endoscope 18 and the connector 18d are made to be detachable, the endoscope 18 can immediately be used when the endoscope 18 is required. After the operation has been completed, the endoscope 18 can quickly be put back. Moreover, exchange to an endoscope 18 having an another observing direction, for example, can easily be performed.

Since the camera head 10 is provided in the endoscope connecting/holding unit 11, a necessity for routing a long cable is not required. Therefore, a plurality of operators are enabled to observe the image obtained by the endoscope and displayed on the monitor.

Moreover, the projection 15a for connecting the holder 15 to the microscope body 4 from outside of the sterilizing drape 16 and the C-shape accommodating portion 15b for holding the endoscope 18 are spatially disposed apart from each other. Therefore, the sterilizing drape 16 is not ripped when the endoscope 18 is joined or removed. If the projection 15a rips the sterilizing drape 16, the sterilization of the endoscope 18 can always be maintained thanks to the spatially distant structure.

[Second Embodiment]

Figure 4:
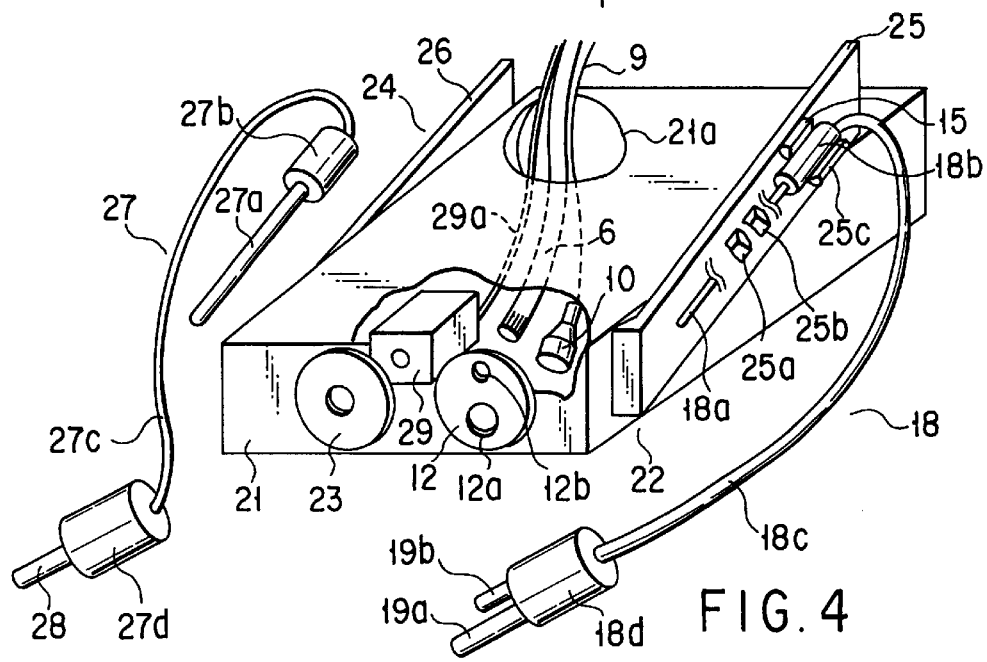
FIG. 4 is a schematic view showing a portion of a microscope apparatus according to a second embodiment.

FIG. 4 shows a second embodiment of the present invention. This embodiment is structured such that an ultrasonic probe serving as the auxiliary observation unit can be connected and held in addition to the endoscope according to the first embodiment. Moreover, the position at which the ultrasonic probe is held can be selected. Note that similar elements to those according to the first embodiment are given the same reference numerals and the similar elements are omitted from description.

An endoscope connecting/holding unit 21 according to this embodiment incorporates the connecting portion comprising the endoscope connecting portion 12 and an ultrasonic (US) probe connecting portion 23. The holding portion of the endoscope connecting/holding unit 21 is constituted by an endoscope holding portion 22 and an US probe holding portion 24.

An endoscope holding portion 22 is disposed in the right-hand portion of FIG. 4. A frame 25 formed upwards from the endoscope connecting/holding unit 21 and the holder 15 secured to the frame 25 constitute the endoscope holding portion 22. The frame 25 has three recesses 25a, 25b and 25c serving as selectable displacement means. In a state shown in FIG. 4, the holder 15 has been pushed into the recess 25c.

The US probe holding portion 24 is disposed in the left-hand portion of FIG. 4. The shape of the US probe holding portion 24 is bilateral symmetrical to the endoscope holding portion 22. The US probe holding portion 24 is constituted by a frame 26 formed upwards from the endoscope connecting/holding unit 21 and the holder 15 (not shown) secured to the frame 26. The frame 26 has three recesses (not shown).

Reference numeral 27 represents an US probe for performing ultrasonic observation. The US probe 27 has an insertion portion 27a and a body 27b. An US cable 27c extends from the body 27b, the US cable 27c having an end provided with a connector 27d. The connector 27d is provided with an US transmission portion 28 comprising a flexible shaft and a transmission mechanism, such as a signal line, for rotating an ultrasonic oscillator provided in the distal end (not shown) of the US probe 27 and transmitting a signal to the ultrasonic oscillator.

The connector 27d of the US probe 27 has a size and a shape with which the connector 27d can be connected to the US probe connecting portion 23 of the endoscope connecting/holding unit 21. The US probe connecting portion 23 accommodates an US drive unit 29 to enable rotating force and a signal to be transmitted to the US transmission portion 28 when the connection with the US probe 27 has been established.

An US cable 29a extends from the US drive unit 29 to the outside of the endoscope connecting/holding unit 21 through an opening 21a similarly to the light guide fiber 6 and the camera cable 9. Then, the US cable 29a passes through an opening (not shown) formed in the lower portion of the microscope body so as to be introduced into the body. Then, the US cable 29a passes through the inside portions of the arm portion and the frame portion so as to be connected to the monitor.

(Operation)

When the operation of the surgical microscope apparatus according to this embodiment is performed, the surgical microscope (not shown) and the endoscope connecting/holding unit 21 are covered with the sterilizing drape 16. Then, the projection 15a of the sterilized holder 15 is, together with the sterilizing drape 16, pushed into any one of the recesses 25a to 25c disposed at a position at which the endoscope 18 can satisfactorily be held. After the connector 18d of the endoscope 18 is connected to the endoscope connecting portion 12, the body 18b of the endoscope 18 is pushed into the C-shape accommodating portion 15b of the holder 15. Thus, the endoscope 18 is held.

Similarly, the projection 15a of the sterilized holder 15 is pushed into a recess in the vicinity of the position at which the US probe 27 is required to be held on the US probe holding portion 24. Then, the connector 27d of the US probe 27 is connected to the US probe connecting portion 23. As a result, transmission of the rotating force and the signal from the US drive unit 29 is permitted.

Then, the body 27b of the US probe 27 is pushed into the C-shape accommodating portion 15b of the holder 15 so that the endoscope 27 is held.

This embodiment is structured such that the endoscope holding portion 22 is disposed in the right-hand portion of the drawing and the US probe holding portion 24 is disposed in the left-hand portion of the drawing. The structure is not limited to the foregoing structure. A reverse arrangement may be employed. Only either of the endoscope holding portion 22 or the US probe holding portion 24 may be disposed or the two holding portions 22 and 24 may be disposed on either side.

Although three recesses are provided in this embodiment, the number is not limited to this. Two or four or more recesses may be provided.

Since also the US probe can be used in addition to the surgical microscope according to the first embodiment, the state of the inside portion of an organization which cannot be observed by the surgical microscope or the endoscope can be observed. Since the position at which the endoscope is held can precisely be set, the position can be set such that the endoscope can naturally be held (without any special consciousness). As a result, an operator is able to focus the energy on performing the operation, causing a satisfactory operation to be performed.

[Third Embodiment]

Figure 5:
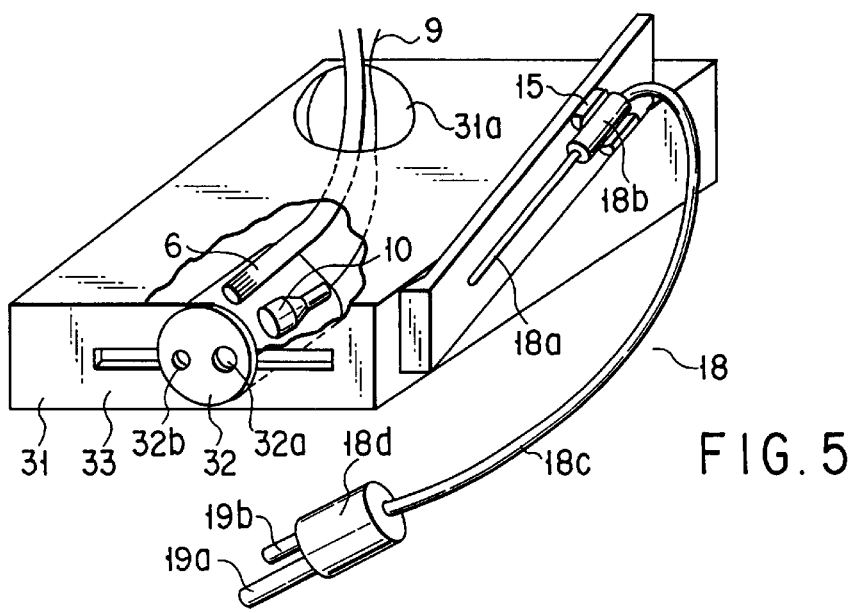
FIG. 5 is a schematic view similar to FIG. 4 and showing a microscope apparatus according to a third embodiment.

FIG. 5 shows a third embodiment. This embodiment is structured such that variation of the position at which the endoscope is connected and which is fixed in the first embodiment is permitted.

An endoscope connecting/holding unit 31 according to this embodiment has an endoscope connecting portion 32 serving as the connecting portion. The endoscope connecting portion 32 is supported such that lateral movement along a groove 33 serving as a displacement means is permitted.

A sterilizing drape (not shown) has perforations formed in the vicinity of the endoscope connecting portion 32 and permitting separation of the sterilizing drape when the connection of the endoscope connecting portion 32 has been established. Looseness with which satisfactory endurance against the right-hand and left-hand movement of the endoscope connecting portion 32 is imparted to the portion around the perforations.

The endoscope connecting portion 32 is provided with an observation-system connecting portion 32a and an illuminating-system connecting portion 32b. The camera head 10 and the light guide fiber 6 are coaxially disposed at the rear of the observation-system connecting portion 32a and the illuminating-system connecting portion 32b. The camera head 10 and the light guide fiber 6 are secured with respect to the observation-system connecting portion 32a and the illuminating-system connecting portion 32b such that their positions are not changed in the endoscope connecting portion.

The camera cable 9 of the camera head 10 and the light guide fiber 6 are disposed such that sufficient looseness is imparted to endure the lateral movement of the endoscope connecting portion 32. The camera cable 9 and the light guide fiber 6 pass though the opening 17 to be extended to the outside of the endoscope connecting/holding unit 11. Then, the camera cable 9 and the light guide fiber 6 pass through an opening (not shown) formed in the lower portion of the microscope body 4 of the surgical microscope apparatus 1 so as to be guided into the microscope body 4.

Referring to FIG. 5, when the surgical microscope (not shown) and the endoscope connecting/holding unit 31 are covered with the sterilizing drape, looseness of the drape caused when the endoscope connecting portion 32 is disposed at an intermediate position is uniformed in the lateral direction. Then, the perforations are teared to connect the connector 18d of the endoscope 18 to the endoscope connecting portion 32.

In the foregoing state, the endoscope connecting portion 32 is slid laterally over the drape to move the endoscope connecting portion 32 at a required position. At this time, the optical connecting systems in the endoscope connecting portion 32 are not moved. Only the light guide fiber 6 and the camera cable 9 are moved. Since the other structures are the same as those according to the first embodiment, the same structures are omitted from description. Although this embodiment has the structure that the endoscope connecting portion 32 is slid laterally, the direction is not limited to this. The endoscope connecting portion 32 may be slid vertically or diagonally.

In addition to the effects obtainable from the first embodiment, the operability can be improved because the cable can be routed to correspond to the type of the operation thanks to the structure that the position of the connecting portion can be varied to permit change in the routing of the cable.

[Fourth Embodiment]

Figure 6:
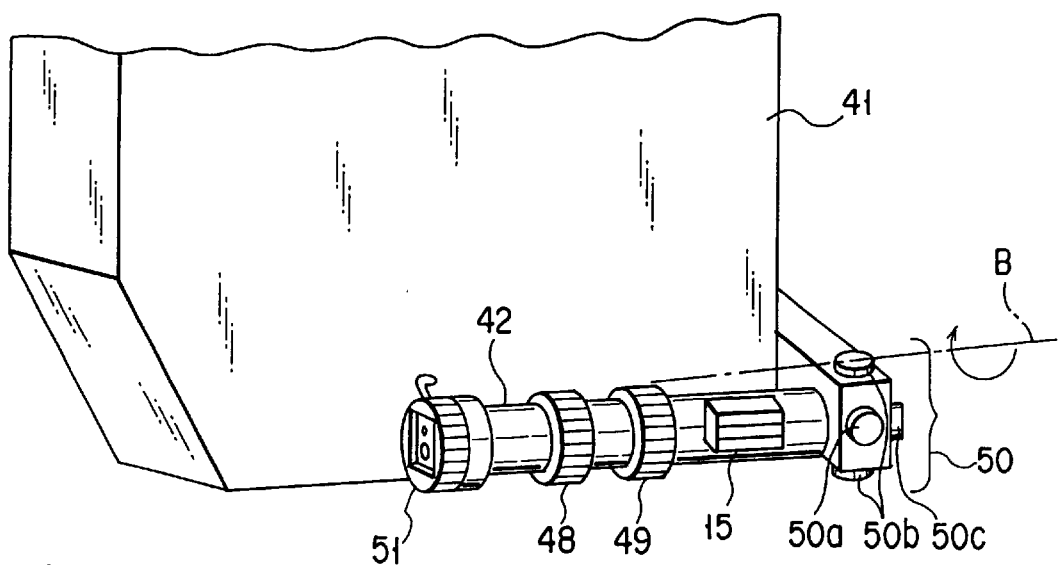
FIG. 6 is a schematic view showing a portion in the vicinity of the microscope body of a microscope apparatus according to a fourth embodiment.
Figure 7:
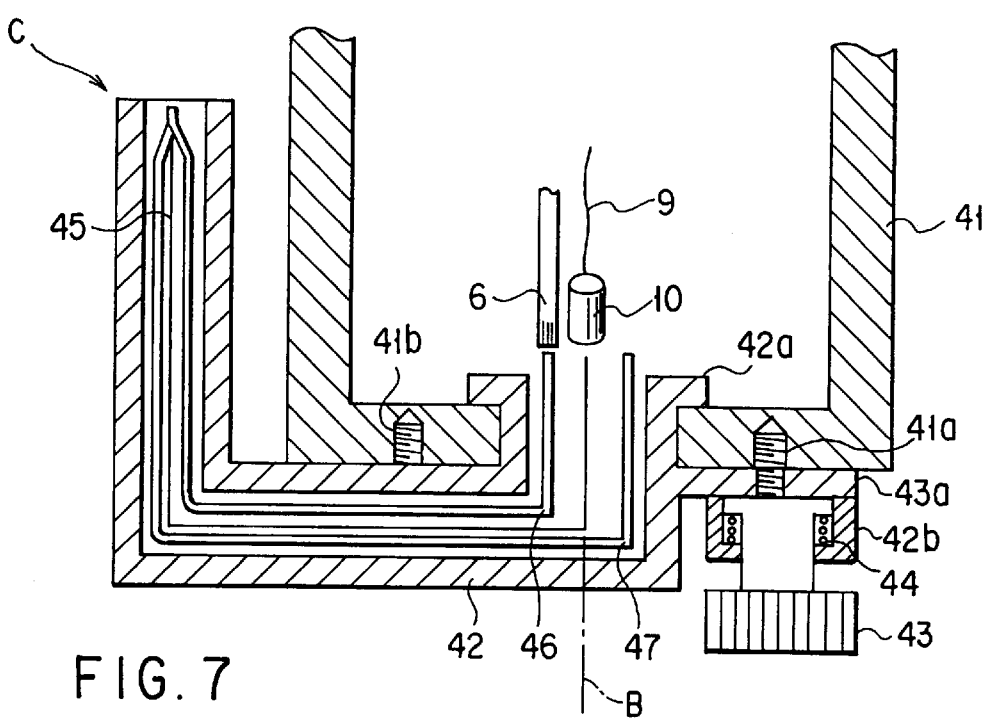
FIG. 7 is a cross sectional view showing the internal structure of a connecting/holding unit joined to the microscope body shown in FIG. 6.
Figure 8:
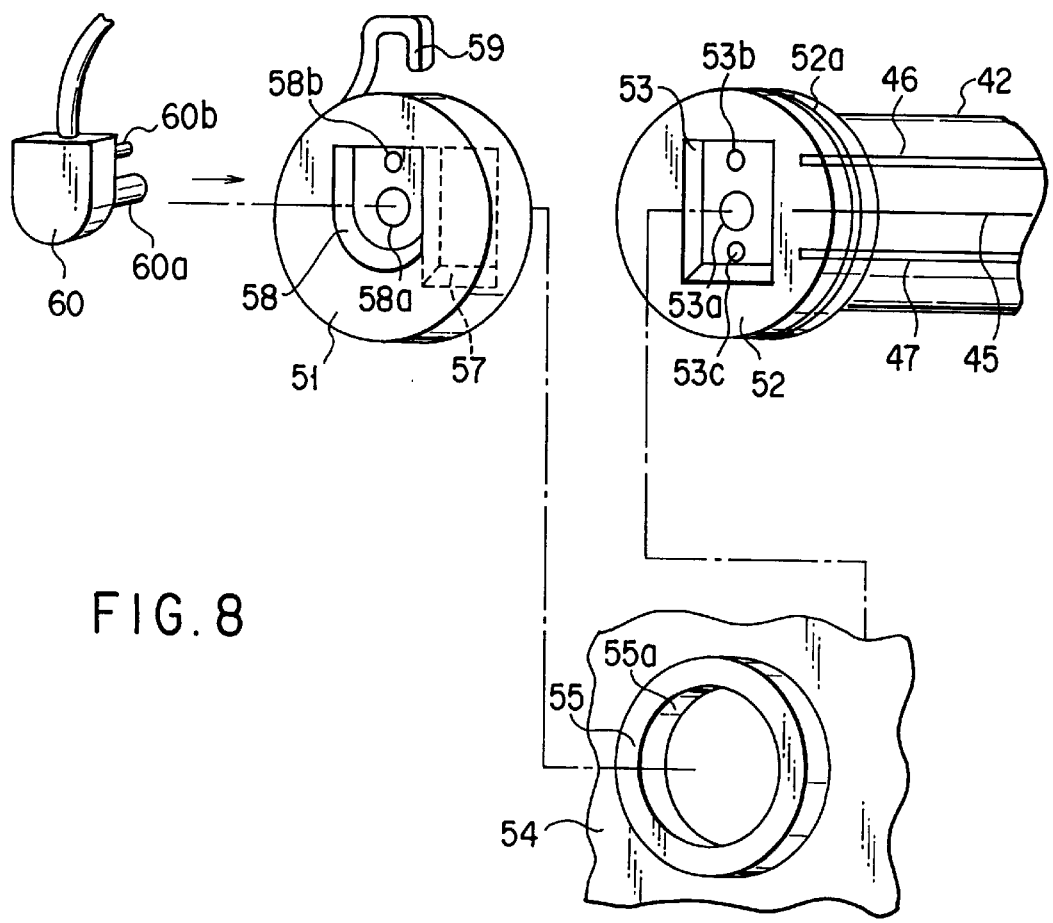
FIG. 8 is a schematic view showing a sterilization adapter joined to the microscope apparatus shown in FIG. 6.

FIGS. 6 to 8 show a fourth embodiment of the present invention. This embodiment has a structure that the endoscope connecting/holding unit can be shifted to an arbitrary side of the two sides of the microscope body. FIG. 6 shows the appearance of the microscope body 41 and the endoscope connecting/holding unit 42. FIG. 7 is a horizontal cross section showing a state where the microscope body 41 and the endoscope 42 are optically and mechanically coupled.

An endoscope connecting/holding unit 42 which is movable or rotatable around a shaft B is supported by the microscope body 41. A flange 42a disposed in the microscope body 41 prevents separation of the endoscope connecting/holding unit 42 from the microscope body 41. Thus, the endoscope connecting/holding unit 42 is able to rotate around the shaft B with respect to the microscope body 41.

Referring to FIG. 7, the endoscope connecting/holding unit 42 is provided with a casing 42b for accommodating a fixing screw 43 for securing the endoscope connecting/holding unit 42 to the microscope body 41. The fixing screw 43 is provided with a flange 43a for preventing separation, the flange 43a being urged to the microscope body 41 by a compression spring 44. Female screws 41a and 41b which are disposed opposite to the fixing screw 43 when the endoscope connecting/holding unit 42 has been brought to a horizontal state are provided on the microscope body 41.

The camera head 10 is disposed on the shaft B in the microscope body 41. An observation optical system 45 (indicated with a thick solid line) constituted by optical elements incorporating a lens and a prism is disposed on the shaft B in the endoscope connecting/holding unit 42 in a direction opposite to the camera head 10. Both of the observation optical system 45 and the camera head 10 are coaxially disposed on the shaft B. Therefore, only the image can be rotated without any eccentricity if the endoscope connecting/holding unit 42 is (on the shaft B) rotated with respect to the microscope body 41. The direction of the observation optical system 45 is changed by an optical elements (not shown), such as a prism, to be guided to the distal end of the endoscope connecting/holding unit 42.

Referring to FIG. 7, the light guide fiber 6 is disposed in a portion on the left-hand side of the shaft B in the microscope body 41. A first light-transmission portion 46 is disposed in the endoscope connecting/holding unit 42 at a position opposite to the light guide fiber 6. A second light-transmission portion 47 is disposed at a position which is point symmetrical to the first light-transmission portion 46 with respect to the shaft B. Each of the light-transmission portions 46 and 47 is constituted by, for example, a single plastic fiber. Also the light-transmission portions 46 and 47 are guided to the distal end of the endoscope connecting/holding unit 42. Thus, the first light-transmission portion 46 is disposed on this side of the drawing sheet and the second light-transmission portion 47 is disposed in back of the drawing sheet. That is, the first light-transmission portion 46 is disposed in the upper portion in FIG. 6 and the second light-transmission portion 47 is disposed in a lower portion in FIG. 6.

When the endoscope connecting/holding unit 42 is disposed with respect to the microscope body 41 at a portion opposite to the position shown in FIGS. 6 and 7, the endoscope connecting/holding unit 42 is rotated by 180° about the shaft B. The light guide fiber 6 is disposed opposite to the second light-transmission portion 47 such that the second light-transmission portion 47 is disposed in the upper portion and the first light-transmission portion 46 is disposed in the lower portion. That is, the light-transmission portion opposite to the light guide fiber 6 is always disposed in the upper portion.

Referring back to FIG. 6, reference numeral 48 represents an image rotating ring for rotating an image transmitted from the observation optical system 45. The image rotating ring 48 rotates an image rotator (not shown) disposed in the observation optical system 45.

Reference numeral 49 represents a zoom ring which moves a zoom lens (not shown) in the observation optical system 45 to enlarge/contract an image. Reference numeral 50 represents an eccentricity adjustment dial incorporating a X-direction adjustment dial 50a, a Y-direction adjustment dial 50b and a Z-direction adjustment dial 50c. To enable the Y-direction adjustment dial 50b to be operated from an upper position even if the Y-direction adjustment dial 50b is rotated in an opposite direction about the shaft B, the Y-direction adjustment dial 50b vertically penetrates the eccentric adjustment dial. The X-direction adjustment dial 50a and the Y-direction adjustment dial 50b move an adjustment lens (not shown) in the observation optical system 45 in the X and Y directions. Thus, the eccentricity of the transmitted image, between the endoscope and the observation optical system 45, can be corrected. The Z-direction adjustment dial 50c moves a focusing lens (not shown) in the observation optical system 45 to adjust the focal point between the endoscope and the observation optical system 45. To enable an operator to intuitively recognize the operation direction, the foregoing dials 50a, 50b and 50c are disposed as shown in FIG. 6. A mechanism portion (not shown), such as a link, moves the lens. Reference numeral 51 represents a sterilizing adapter serving as a connecting portion.

FIG. 8 is a diagram showing the connection established in the vicinity of the sterilizing adapter 51.

A sterilizing adapter connecting portion 52 is formed at the distal end of the endoscope connecting/holding unit 42. The sterilizing adapter connecting portion 52 has a rectangular recess 53. An observation light incident portion 53a, a first light emission end 53b and the second light emission end 53c are provided for the inside portion of the rectangular recess 53. An observation optical system 45, a first light-transmission portion 47 and a second light-transmission portion 46 are formed at the rear ends of the corresponding portions. A projection 52a is formed over the outer surface of the sterilizing adapter connecting portion 52.

Reference numeral 54 represents a sterilizing drape for covering the microscope body 41 and the endoscope connecting/holding unit 42. A joining ring 55 made of elastic material is joined to the sterilizing adapter connecting portion 52. A groove 55a is formed in the inner surface of the joining ring 55.

The sterilizing adapter 51 is made of material, such a stainless steel, which is able to endure high-pressure steam sterilization and EOG (Ethylene Oxide Gas) sterilization. The sterilizing adapter 51 has a rectangular projection 57, a U-shape recess 58 and a hook 59. An observation light emission end 58a and an illuminating light emission end 58b are disposed in the U-shape recess 58. The observation light emission end 58a and the illuminating light emission end 58b are provided with cover glass members (not shown). The observation light incident portion 53a, the first light emission end 53c and the second light emission end 53c are unclean portions because the foregoing portion cannot be sterilized. The foregoing cover glass members insulate the foregoing unclean portions from the observation-system connecting portion and the illumination-system connecting portion of the endoscope connector which must be sterilized to be clean portions.

Reference numeral 60 represents an endoscope connector having a shape which is able to engage to the U-shape recess 58 of the sterilizing adapter 51. The endoscope connector 60 incorporates an observation-system connecting portion 60a and an illuminating-system connecting portion 60b. The endoscope connector 60 of the endoscope has a shape with which the endoscope connector 60 is engaged to the U-shape recess 58 from only one direction. On the other hand, the rectangular projection 57 of the sterilizing adapter 51 can be engaged to the rectangular recess 53 of the sterilizing adapter connecting portion 52 from two directions when the rectangular projection 57 is turned upside down.

(Operation)

When an operation is performed, the portion in which the endoscope connecting/holding unit 42 is disposed with respect to the endoscope connecting/holding unit 42 is determined. An assumption is made that the portion shown in FIG. 6 is selected. When the endoscope connecting/holding unit 42 is rotated to be horizontal as shown in FIG. 7, the distal end of the fixing screw 43 is introduced owing to the urging force of the compression spring 44 at the position of the female screw 41*a*. When the fixing screw 43 is screwed in the foregoing state, the endoscope connecting/holding unit 42 is secured to the microscope body 41.

In the foregoing state, the first light-transmission portion 46 is opposite to the light guide fiber 6, as shown in FIG. 7. The first light-transmission portion 46 is connected to the first light emission end 53*c*. That is, light is emitted from the first light emission end 53*c*.

Then, the sterilizing drape 54 shown in FIG. 8 is joined to the sterilizing adapter connecting portion 52. The groove 55*a* in the joining ring 55 is engaged to the projection 52*a* so that sterilizing drape 54 is joined as described above.

In the foregoing state, the sterilizing adapter 51, which has been sterilized, is joined to the sterilizing adapter connecting portion 52 such that the hook 59 faces upwards.

Hence it follows that the illuminating light emission end 58*b* disposed in the U-shape recess 58 and the first light emission end 53*b* are connected to each other. When the endoscope connector 60 is connected to correspond to the U-shape recess 58 of the sterilizing adapter 51, the illuminating-system connecting portion 60*b* and the illuminating light emission end 58*b* are connected to each other. Thus, light transmitted through the light guide fiber 6 is guided to the illuminating-system connecting portion 60*b* so that illumination is performed from the distal end of the endoscope. Note that the cable of the endoscope is hooked on the hook 59, if necessary.

When another operation is performed such that the endoscope connecting/holding unit 42 is set with respect to the microscope body 41 in a reversed manner to that shown in FIG. 6, the following operations are performed before the sterilizing drape is set.

The fixing screw 43 shown in FIG. 7 is loosened so as to be removed from the female screw 41*a*. The endoscope connecting/holding unit 42 is rotated about the shaft B. The fixing screw 43 is introduced at the position of the female screw 41*b*. When the fixing screw 43 is similarly screwed, the endoscope connecting/holding unit 42 is secured. The second light-transmission portion 47 is disposed opposite to the light guide fiber 6 after the endoscope connecting/holding unit 42 has been rotated by 180°. As a result of the rotation by 180°, the second light-transmission portion 47 and the second light emission end 53*c* are disposed at upper positions. In the foregoing case, the sterilizing drape 54 is set and the cable hook of the sterilizing adapter 51 is joined to face upwards so that the endoscope connector 60 is connected.

Light emitted through the light guide fiber 6 is guided to the illuminating-system connecting portion 60*b* through the second light-transmission portion 47, the second light emission end 53*b* and the illuminating light emission end 58*b* so as to be emitted from the distal end of the endoscope.

Then, whether or not the image observed with the endoscope is eccentric is confirmed. If the eccentricity is detected, the X-direction adjustment dial 50*a* and the Y-direction adjustment dial 50*b* of the eccentricity adjustment dial 50 are rotated to move the lens (not shown). Thus, adjustment is performed in such a manner that the observed image is positioned at the center of the monitor. Then, whether or not focusing is adequate is confirmed. If blur is detected, adjustment is performed by operating the Z-direction adjustment dial 50*c*.

After the foregoing adjustment operations have been completed, the scope is used to observe the portion to be operated.

When the image displayed on the monitor has been rotated with respect to the direction of the field of view, the image rotating ring 48 is rotated to adjust the direction. If an inadequate magnification is employed, the zoom ring 49 is rotated to adjust the magnification.

When the endoscope is not operated, the endoscope is held by the holder 15. When another endoscope having a difference direction of the field of view is employed, the endoscope connector 60 is removed and the endoscope connector of the other endoscope is connected. The endoscope connector is connected to the unclean endoscope connecting/holding unit 42, which cannot be sterilized, through the clean sterilizing adapter 56 which can be sterilized. Therefore, the endoscope connector, which is always cleaned, can easily be changed.

In addition to the effect obtainable from the surgical microscope according to the first embodiment, the connection and holding of the endoscope can satisfactorily be performed by the dominant arm of the operator because the endoscope connecting/holding unit 42 can considerably be moved to the two sides of the microscope body 41 about the shaft B. Since the sterilizing adapter 56 is used, change of the endoscope can be performed during the operation.

[Fifth Embodiment]

Figure 9:
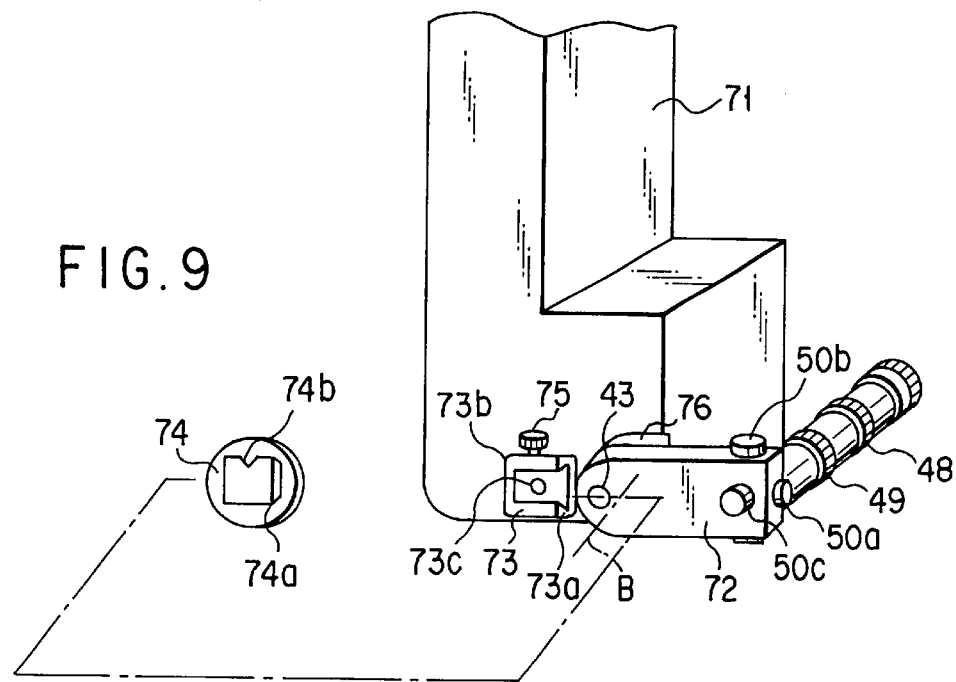
FIG. 9 is a diagram showing a portion of a microscope apparatus according to a fifth embodiment which incorporates a detachable connecting/holding unit for the endoscope.

FIG. 9 shows a fifth embodiment. This embodiment is a modification of the fourth embodiment in which the endoscope connecting/holding unit is made to be detachable with respect to the microscope body.

A microscope body 71 is provided with a connecting portion 73 which accurately connect the endoscope connecting/holding unit 72. The connecting portion 73 incorporates a pair of guide rails between which a dovetail groove 73*a* is formed and each of which has a trapezoidal shape in a cross section; a stopper 73*b* and an urging screw 75. Moreover, the connecting portion 73 incorporates an opening 73*c* which permits passage through an optical system (not shown) in the microscope body 71 and an optical system (not shown) in the endoscope connecting/holding unit 72 without any interruption.

Reference numeral 74 represents a cover. A dovetail tenon 74*a* incorporating a rail having a trapezoidal cross sectional shape projects over the cover 74. A V-groove 74*b* is provided for the dovetail tenon 74*a* at a position which is pressed by the urging screw 75. Although the cover 74 is illustrated such that the dovetail tenon 74*a* is disposed on this side to cause the shape of the dovetail tenon 74*a* to easily be understood, the dovetail tenon 74*a* faces the opposite direction in a joined state.

The endoscope connecting/holding unit 72 is provided with a joining frame 76. The joining frame 76 and the endoscope connecting/holding unit 72 hold the relationship that rotation about the shaft B is permitted and movement in the axial direction is inhibited. Reference numeral 43 represents a fixing screw for securing the joining frame 76 and the endoscope connecting/holding unit 72 at two points apart from each other by 180°. Since the specific structures are the same as those of the microscope body and the endoscope connecting/holding unit according to the fourth embodiment, the structures are omitted from description. The surface of the joining frame 76 in the lower of the drawing sheet (a portion in the vicinity of the microscope body) is provided with a dovetail tenon and a V-groove which are the same as those of the cover 74.

(Operation)

When the endoscope is not used together with the surgical microscope, the dovetail tenon 74*a* of the cover 74 is inserted into the dovetail groove 73*a* provided for the microscope body 71 such that the dovetail tenon 74*a* is inserted toward the lower portion of the drawing sheet from a right-hand position in the drawing sheet. After the dovetail tenon 74*a* has been inserted as described above, the urging screw 75 downwards urges the projection 74*a* against the dovetail groove 73*a*. The urging screw 75 is disposed at the position at which the urging screw 75 presses the inclined surface of the V-groove 74*b* so that urging screw 75 urges the dovetail groove 73*a* to the lower portion and the left-hand portion in the drawing. Hence it follows that the dovetail tenon 74*a* is pressed against the guide rail below the dovetail groove 73*a* and the stopper 73*b* so as to be connected as described above.

When both of the surgical microscope and the endoscope are used, a reverse procedure is performed. That is, the cover 74 is removed, and then the dovetail tenon of the endoscope connecting/holding unit 72 is similarly connected. Since the connection is established by using the dovetail joint, the connection can be established with excellent position accuracy. After the connection has been established, transmission through the optical system is permitted through the opening 73*c*. The other structures are the same as those according to the fourth embodiment. Therefore, description of the other structures is omitted.

In this embodiment, the direction in which the endoscope is connected is the forward direction with respect to the microscope body (the back of the drawing sheet in FIG. 9). The direction is not limited to the foregoing direction. The connection may be established in the rearward direction of the microscope body (toward this side of the drawing sheet).

In this embodiment, the distal end of the dovetail tenon (the insertion portion) is brought into contact with the abutting portion on the left side of the dovetail groove. The structure is not limited to the foregoing structure. The two ends of the drive groove may be formed into the stopper portions to which the rear end of the dovetail tenon (the insertion portion) is brought into contact with the stopper portions. When the foregoing structure is employed, the dovetail tenon can be inserted into the dovetail groove from either of the right position or the left position. If the endoscope connecting/holding unit has no rotating mechanism, the endoscope connecting/holding unit can be shifted to either of the right and left sides with respect to the microscope body.

When the endoscope is not used, the endoscope connecting/holding unit 72 can be removed from the microscope body 71. Therefore, excessive occupation of the space can be prevented and a wide space for performing an operation can be obtained. Since the endoscope connecting/holding unit 72 can be removed, the weight of the microscope body 71 can be reduced. Thus, handling easiness can be improved.

[Sixth Embodiment]

Figure 10:
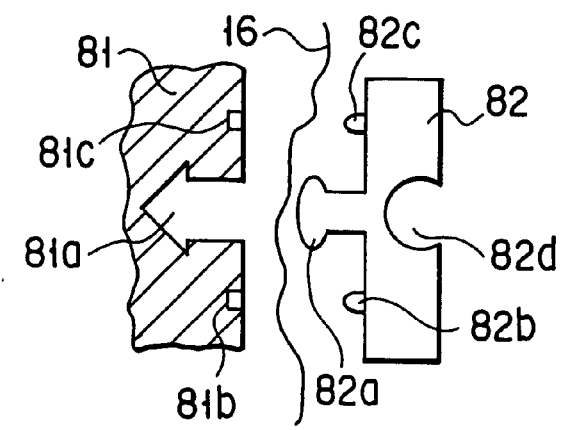
FIG. 10 is a diagram showing a microscope apparatus according to a sixth embodiment and having a changed holding portion.

FIG. 10 shows a sixth embodiment of the present invention. This embodiment is a modification of the joining portion according to the first embodiment. Since the structures except for the joining portion are the same as the first embodiment, only the relationship between the joining portion and the endoscope connecting/holding unit will now be described.

The endoscope connecting/holding unit 81 has a joining recess 81*a*. Sub-recesses 81*b* and 81*c* are formed around the joining recess 81*a*. Reference numeral 16 represents a sterilizing drape. On the other hand, the holder 82 has a joining projection 82*a*. Sub-projections 82*b* and 82*c* are formed around the joining projection 82*a*. The holder 82 has a C-shape accommodating portion 82*d* for holding an endoscope (not shown).

(Operation)

When the surgical microscope apparatus is used, the endoscope connecting/holding unit 81 is covered with the sterilizing drape 16. Then, the holder 82 is joined. In the foregoing case, the joining projection 82*a* and the sterilizing drape 16 are inserted into the joining recess 81*a*. Thus, the holder 82 is secured to the endoscope connecting/holding unit 81. The sub-projection 82*b* is inserted into the sub-recess 81*b*, while the sub-projection 82*c* is inserted into the sub-recess 81*c*.

If the sterilizing drape 16 is ripped in the portion between the joining projection 82*a* and the joining recess 81*a* in which the sterilizing drape 16 is deformed in a large quantity, the sterilizing drape 16 is held between the adjacent sub-projection 82*b* and the sub-recess 81*b* and between the sub-projection 82*c* and the sub-recess 81*c*. Therefore, exposure of an unclean portion of the endoscope connecting/holding unit 81 over the ripped portion of the drape can be prevented.

The number of each of the sub-recesses and sub-projections is not limited to two. The number may be one or three or more.

In addition to the effect obtainable from the first embodiment, a clean environment can be maintained because the endoscope connecting/holding unit 81 and the holder 82 are secured to each other even if the sterilizing drape 16 is ripped.

[Seventh Embodiment]

Figure 11:
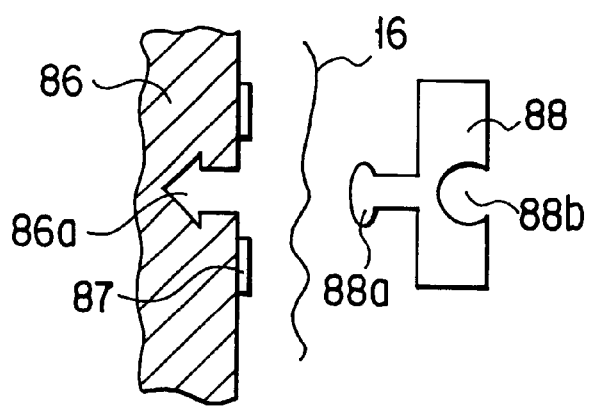
FIG. 11 is a diagram showing a microscope apparatus according to a seventh embodiment and having a changed holding portion.

FIG. 11 shows a seventh embodiment of the present invention. This embodiment is a modification of the sixth embodiment.

An endoscope connecting/holding unit 86 has a joining recess 86*a*. Either side of an annular double-sided adhesive tape 87 is bonded to the portion around the joining recess 86*a*. Note that reference numeral 16 represents a sterilizing drape. On the other hand, the holder 88 has a joining projection 87*a* and a C-shape accommodating portion 88*b* for holding an endoscope (not shown).

(Operation)

Similarly to the sixth embodiment, when the apparatus is used, the endoscope connecting/holding unit 86 is covered with the sterilizing drape 16. Then, the holder 88 is secured.

The joining projection 88*a* is depressed so that the joining projection 88*a* and the sterilizing drape 16 are inserted into the joining recess 86*a*. Thus, the holder 88 is secured to the endoscope connecting/holding unit 86. At this time, the sterilizing drape 16 is pressed against the surface the double-sided adhesive tape 78 by holder 88 so that the sterilizing drape 16 adheres to the endoscope connecting/holding unit 86.

If the sterilizing drape 16 is ripped between the joining projection 88*a* and the joining recess 86*a* in which the sterilizing drape 16 is deformed greatly, the sterilizing drape 16 in the vicinity of the ripped portion adheres to the adjacent double-sided adhesive tape 78. Therefore, an unclean portion of the endoscope connecting/holding unit 86 does not exposed to the outside over the ribbed portion.

Note that the shape of the double-sided adhesive tape 78 is not limited to the annular shape. A plurality of small double-sided adhesive tapes 78 may be disposed around the joining recess 86a. If the adhesiveness of the double-sided adhesive tape 78 deteriorates, change may be permitted. As an alternative to the double-sided adhesive tape, a magic tape may be provided on each of the endoscope connecting/holding unit 86 and the sterilizing drape 16 or each of the sterilizing drape 16 and the holder 88.

Similarly to the sixth embodiment, the sterilizing drape 16 is secured between the endoscope connecting/holding unit 86 and the holder 88. Therefore, a clean environment can be maintained if the sterilizing drape 16 is ribbed.

[Eighth Embodiment]

Figure 12:
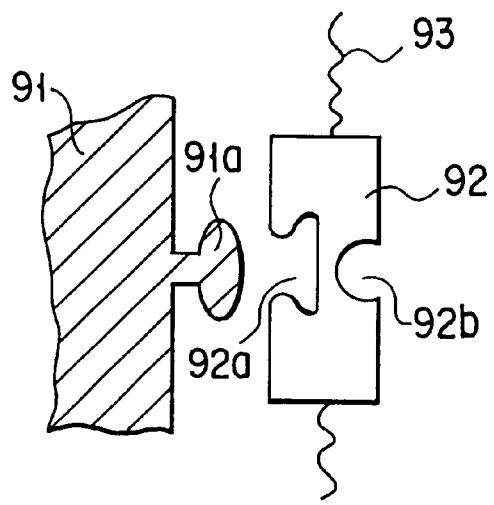
FIG. 12 is a diagram showing a microscope apparatus according to an eighth embodiment and having a changed holding portion.

FIG. 12 shows an eighth embodiment of the present invention. This embodiment is a modification of the sixth embodiment.

An endoscope connecting/holding unit 91 according to this embodiment incorporates a joining projection 91a having a constriction at an intermediate position thereof. On the other hand, the holder 92 has a joining recess 92a and a C-shape accommodating portion 92B for holding an endoscope (not shown). Note that a sterilizing drape 93 is integrally molded with the holder 92.

(Operation)

The endoscope connecting/holding unit 91 is covered with the sterilizing drape 93. Then, the holder 92 is secured. When the joining projection 91a is inserted into the joining recess 92a, the holder 92 is secured to the endoscope connecting/holding unit 91. Since no force is exerted on the sterilizing drape 93, the sterilizing drape 93 is not ribbed.

In this embodiment, the securing process using the sub-projection or the double-sided adhesive tape is not required. Therefore, preparation for the operation can quickly be completed.

[Ninth Embodiment]

Figure 13:
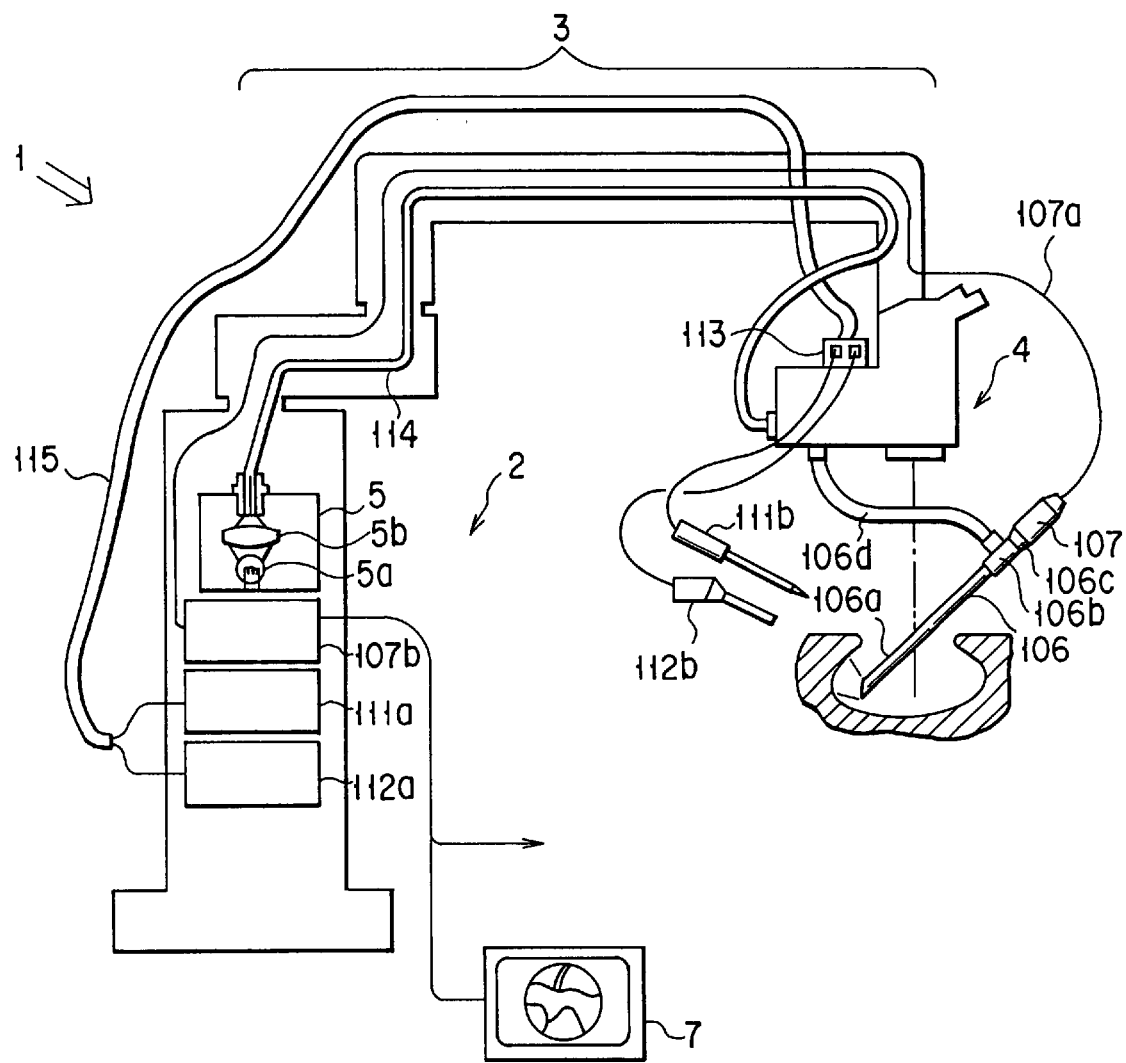
FIG. 13 is a diagram schematically showing the structure of a surgical microscope apparatus according to a ninth embodiment.
Figure 14:
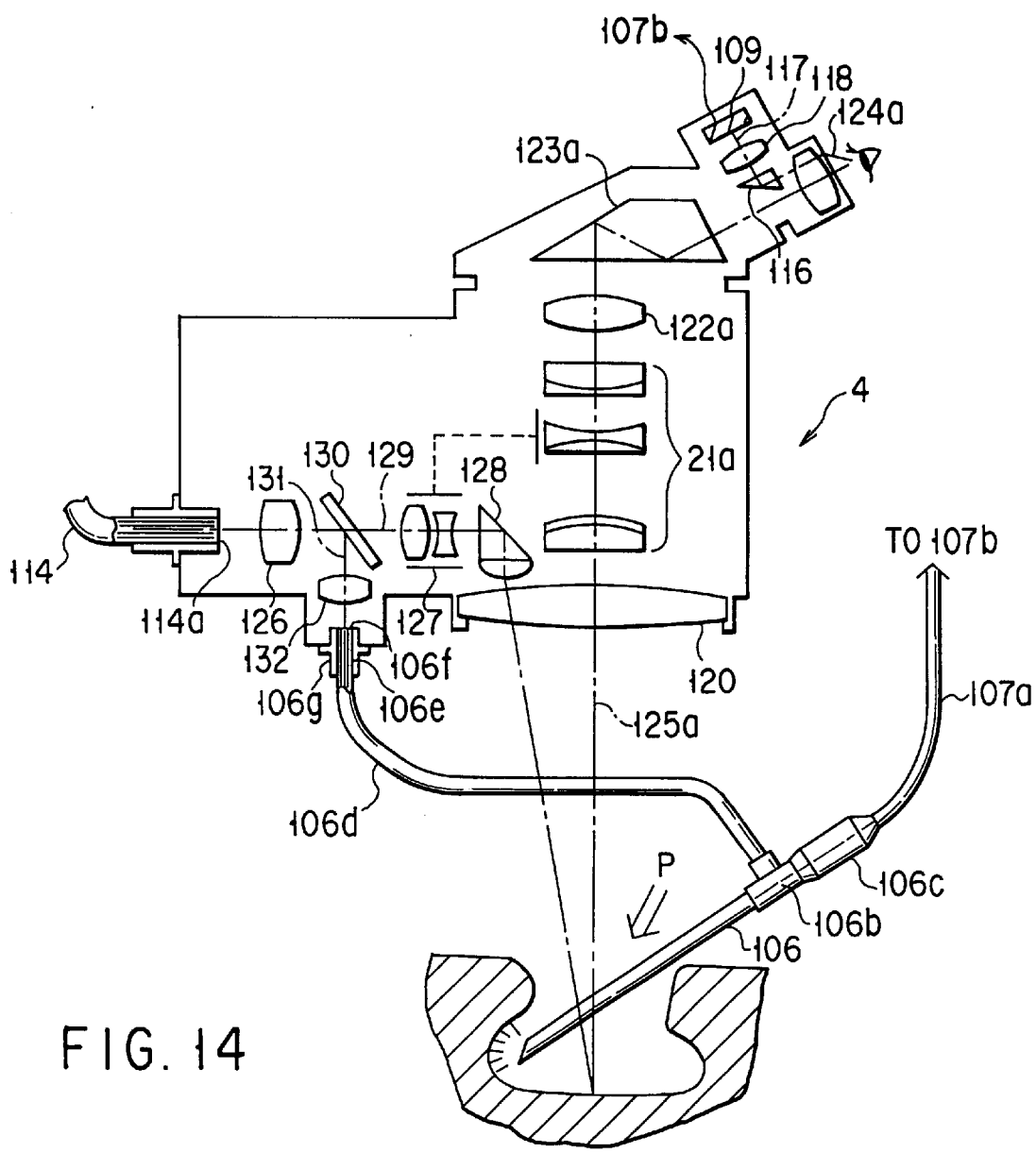
FIG. 14 is a diagram schematically showing the structure in the vicinity a microscope body of the surgical microscope apparatus shown in FIG. 13.
Figure 15:
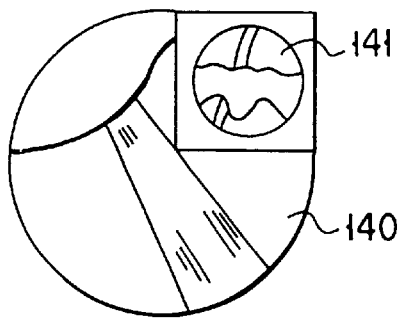
FIG. 15 is a diagram showing a field of view of a microscope of the surgical microscope apparatus shown in FIG. 13.

Referring to FIGS. 13 to 15, a ninth embodiment of the present invention will now be described.

FIG. 13 schematically shows a surgical microscope system incorporating an endoscope. Referring to FIG. 13, reference numeral 1 represents a surgical microscope apparatus. The surgical microscope apparatus 1 incorporates a frame portion 2 disposed on a floor, an arm portion 3 connected to the frame portion 2 and a microscope body 4 supported by the arm portion 3. The microscope body 4 enlarges the image of a portion to be operated so that observation of the portion is permitted. The microscope body 4 is supported by the arm portion 3 such that three-dimensional movement and inclination of the microscope body 4 in a space are permitted. A light source unit 5 is disposed in the support column of the frame portion 2. The light source unit 5 incorporates a lamp 5a and a converging lens 5b. The light source unit 5 emits light which is made incident on a flexible light guide fiber 114 to be described later and disposed in the frame portion 2 and the arm portion 3. Light made incident on the light guide fiber 114 is guided to the microscope body 4 through the light guide fiber 114.

An endoscope 106 for observing a blind spot in the observation field of view for the microscope body 4 is connected to the surgical microscope apparatus 1. The endoscope 106 incorporates an insertion portion 106a and a handy portion 106b. The handy portion 106b incorporates an ocular portion 106c and a light guide cable 106d. A TV camera head 107 is connected to the ocular portion 106c of the endoscope 106. A TV camera cable 107a of the TV camera head 107 is guided into the arm portion 3 and the frame portion 2 so as to be connected to a camera control unit 107b disposed in the frame portion 2. The camera control unit 107b is connected to a monitor 7 and a small-size monitor 109 accommodated in the microscope body 4 as described later.

A light guide fiber 106e is accommodated in the light guide cable 106d of the endoscope 106. The light guide cable 106d is connected to a lower surface of the microscope body 4. Thus, light made incident on the light guide fiber 106e is introduced into the endoscope 106 so as to be applied to the portion, to be operated, through the distal end of the insertion portion 106a.

The frame portion 2 accommodates an electric knife which is an operating tool for treating the portion, to be operated, a power source 111a for an ultrasonic suction unit and a control unit 112a. A cable extending from the body of the power source 111a and that extending from the body of the control unit 112a are bundled into one flexible comprehensive cable 115 so as to be connected to the microscope body 4. The microscope body 4 has a relay unit 113. The flexible comprehensive cable 115 is connected to the relay unit 113. A hand piece 111b of the electric knife and a hand piece 112b of the ultrasonic suction unit are connected to the relay unit 113 so as to electrically be connected to the power source 111a and the control unit 112a.

Referring to FIG. 14, the specific structure of the microscope body 4 will now be described. In the microscope body 4, there are sequentially disposed, from the portion P to be operated, an objective lens 120, a pair of zoom lenses 121a and 121b disposed apart from each other for a certain distance in a direction perpendicular to the surface of the drawing sheet, a pair of image-forming lenses 122a and 122b, a pair of prisms 123a and 123b and a pair of ocular lenses 124a and 124b. Thus, two observing optical passages 25a and 25b for permitting stereomicroscopical observation are formed in the direction perpendicular to the surface of the drawing sheet. Note that elements 121 to 125 for the observing optical passages 125a and 125b having a given suffix b are omitted from illustration.

A light synthesizing prism 116 is provided for the observing optical passage 125a at a position between the prism 123a and the ocular lens 124a. Thus, an optical passage 117 for displaying the inside portion of the field of view is formed. An image-forming lens 118 and the small-size monitor 109 are disposed on the optical passage 117 for displaying the inside portion of the field of view in this sequential order from the light synthesizing prism 116. The small-size monitor 109 is connected to the camera control unit 107b.

A light emission end 114a of the flexible light guide fiber 114 is provided in the microscope body 4. Moreover, an illuminating optical passage 129 for the microscope is formed through a converging lens 126, an illuminating zoom lens 127, an illuminating prism 128 and the objective lens 120 from the light emission end 114a. The illuminating zoom lens 127 is moved in synchronization with the zoom lens 121a of the observing optical passage 125a. The illuminating range realized by the illuminating optical system of the illuminating zoom lens 127 varies according to the size of the observation field of view.

A half mirror 130 is disposed at an intermediate position of the illuminating optical passage 129 for the microscope. The half mirror 130 forms an endoscope illuminating optical passage 131 branched from the illuminating optical passage 129 for the microscope. The half mirror 130 forms a light branching means which splits light transmitted through the illuminating optical passage 129 for the microscope at the ratio of the brightness and guide a portion of split light into the endoscope illuminating optical passage 131. A converging lens 132 is disposed in the endoscope illuminating optical passage 131 to make split light incident on an incident end 106f of the light guide fiber 106e which is a flexible light transmission means disposed in the light guide cable 106d of the endoscope 106.

A connector 106g having a thread formed on the outer surface thereof is provided on the incident end of the light guide cable 106d of the endoscope 106. The connector 106g is used to detachably connect the light guide cable 106d of the endoscope 106 to the microscope body 4.

(Operation)

Light emitted from the light source unit 5 in the frame portion 2 of the surgical microscope apparatus 1 is guided to the light emission end 114a in the microscope body 4 through the light guide fiber 114. Then, light is guided from the light emission end 114a to pass through the converging lens 126, the illuminating zoom lens 127, the illuminating prism 128 and the objective lens 120 so as to be introduced into the portion P to be operated. Light reflected by the portion P to be operated is allowed to pass through the objective lens 120, the pair of the zoom lenses 121a and 121b, the pair of the image-forming lens 122a and 122b, the pair of the prisms 123a and 123b and the pair of the ocular lenses 124a and 124b so as to be introduced into the eyes of the operator. Thus, the portion P to be operated can stereoscopically be observed.

As for light allowed to pass through the illuminating optical passage 129 for the microscope, a portion of reflected light is split by the half mirror 130. Split light is introduced into the endoscope illuminating optical passage 131 so as to be guided to the light guide fiber 106e of the light guide fiber 6 by the converging lens 132 of the endoscope illuminating optical passage 131.

Thus, the portion P to be operated, that is, the portion which must be observed with the light guide fiber 6, is irradiated with light emitted from the distal end of the endoscope 106. An image observed with the endoscope 106 is introduced into the TV camera head 107, the TV camera cable 107a and the camera control unit 107b so as to be displayed on the monitor 7 and the small-size monitor 109 in the microscope body 4. The image displayed on the small-size monitor 109 is supplied to the observing optical passages 125a and 125b through the optical passage 117 for displaying the inside portion of the field of view so as to be introduced into the eye of the operator. Hence it follows that an endoscope image 141 is displayed in a portion of an image region of the field of view 140 of the microscope, as shown in FIG. 15.

According to this embodiment, the light guide cable 106d of the endoscope 106 is connected to the lower surface of the microscope body 4. Therefore, the length of the light guide cable 106d can be minimized. Thus, the light guide cable 106d does not obstruct the operation of the operator. Since the light guide cable 106d is made to be detachable with respect to the microscope body 4, removal of the light guide cable 106d is permitted if the light guide fiber 6 is not used. Therefore, the light guide cable 106d does not obstruct the operation. Moreover, another type endoscope 106 may be employed to be adaptable to the type of the operation.

This embodiment has the structure that the power source 111a and the control unit 112a which are the bodies of the operation tool for treating the affected part when the operation is performed are accommodated in the frame portion 2 of the surgical microscope apparatus 1. The foregoing elements may be accommodated on the wall of the operation room. Moreover, the relay unit is disposed in the lower portion of the operation frame 2 through the unified comprehensive cable. In addition, the hand piece of the operation tool is connected to the relay unit. Note that the means for optically splitting the optical passage may be a beam splitter as a substitute for the half mirror.

[Tenth Embodiment]

Figures 16, 17:
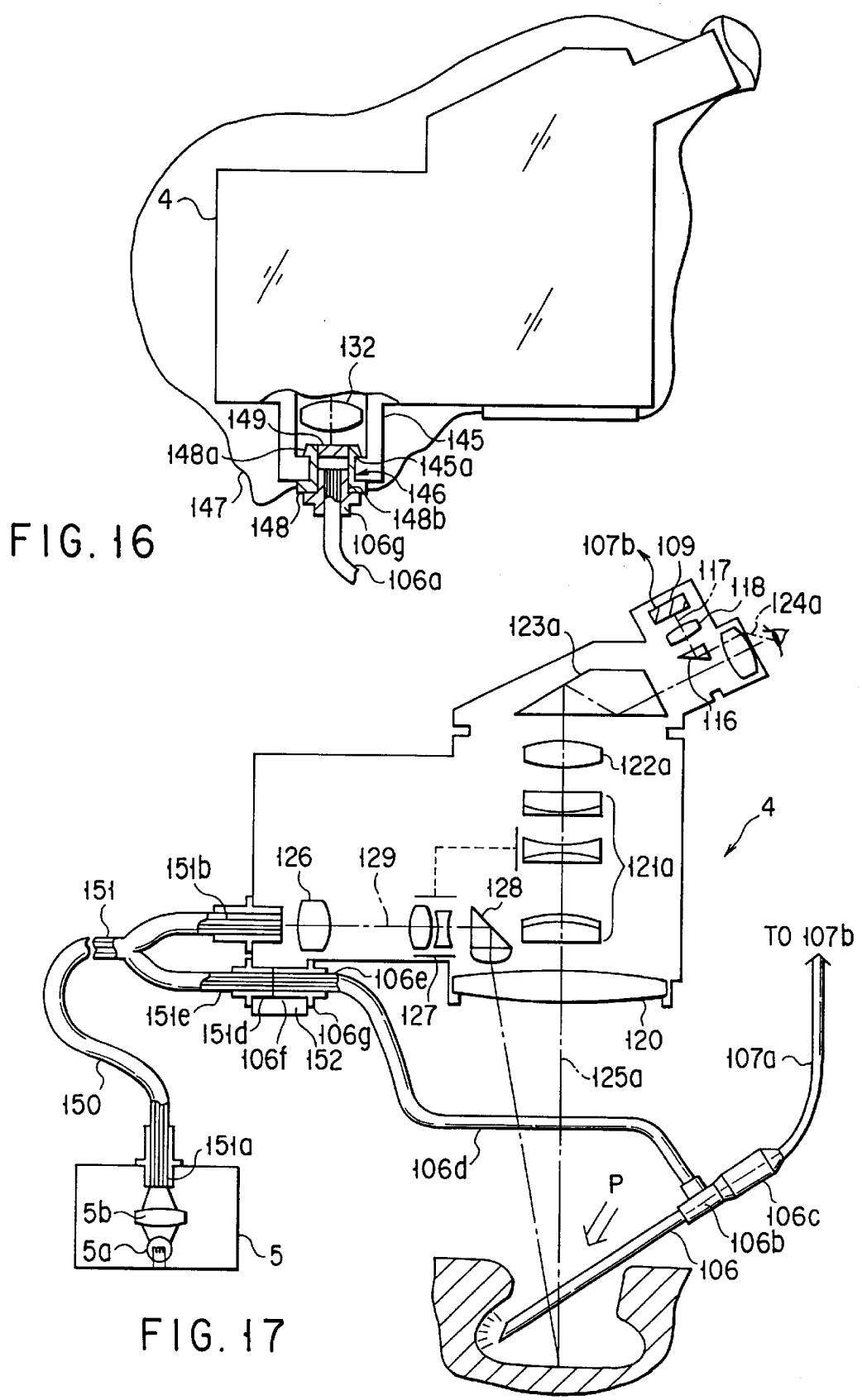
FIG. 16 is a diagram schematically showing a portion of a surgical microscope apparatus according to a tenth embodiment.
FIG. 17 is a diagram schematically showing the structure of a surgical microscope apparatus according to an eleventh embodiment.

Referring to FIG. 16, a tenth embodiment of the present invention will now be described.

The tenth embodiment is a modification of the surgical microscope according to the ninth embodiment in a case where the surgical microscope apparatus 1 is covered with a sterilized transparent bag generally called a "drape".

In the foregoing case, a connecting portion provided for the microscope body 4 for the purpose of connecting the light guide cable 106d of the endoscope 106 is structured as shown in FIG. 16. That is, the connecting pipe 145 formed into a cylindrical shape is secured to the lower portion of the microscope body 4. The connecting pipe 145 accommodates a sterilized converging lens 132 of the endoscope illuminating optical passage 131. The connecting pipe 145 projects over the lower surface of the microscope body 4. A drape joining opening 146 is formed at the projection end of the connecting pipe 145. A sterilized connecting port 148 of the drape 147 is inserted into the drape joining opening 146.

The drape 147 is constituted by a transparent bag having a small thickness which is capable of covering the microscope body 4. The drape 147 has a connecting port 148 formed into a cylindrical shape at a position corresponding to the connecting pipe 145. The connecting port 148 is made of elastic material and formed into a cylindrical shape. The connecting port 148 penetrates a portion of the drape 147 so as to hermetically be secured to the drape 147.

An end flange 148a is provided on an insertion end (the inside portion) of the connecting port 148. The end flange 148a is engaged with a stepped portion 145a formed at the inner end of the drape joining opening 146 of the connecting pipe 145 when the connecting port 148 has been inserted into the drape joining opening 146. Thus, separation of the connecting port 148 inserted into the drape joining opening 146 can be prevented.

A thread 148b is provided on the inner surface of the connecting port 148. The thread 148b is engaged with a thread portion (not shown) provided on the connector 106g of the light guide cable 106d for the endoscope.

An optical member 149 which permits penetration of light and which has been sterilized adheres to the inner end of the connecting port 148 so as to hermetically be secured. The optical member 149 is made of synthetic resin or glass.

Therefore, when the microscope body 4 is covered with the drape 147, the sterilized state of the microscope body 4 can be maintained. In general, the light guide cable 106d of the endoscope 106 is sterilized with high-pressure steam. The light guide cable 106d is connected to the microscope body 4 through the sterilized connecting port 148. Therefore, the sterilized state of the microscope body 4 can be maintained. If the light guide cable 106d of the endoscope 106 is removed, unclean matter does not dropped to the portion, which must operated, because the microscope body 4 is separated from outside by the optical member 149.

[Eleventh Embodiment]

Referring to FIG. 17, an eleventh embodiment of the present invention will now be described.

This embodiment is different from the ninth embodiment in the structure of the illuminating optical passage 129 for the microscope and the endoscope illuminating optical passage 131. The other structures are the same as those of the ninth embodiment.

FIG. 17 shows the structures of the microscope body 4 and its peripheral equipment. Referring to FIG. 17, reference numeral 150 represents a light guide cable which accommodates a light guide fiber 151 divided into two pieces. The incident portions of the light guide fiber 151 are bundled into one piece. The incident end 151a bundled into one piece is connected to the light source unit 5 similarly to the ninth embodiment.

The emission portion of the light guide fiber 151 is branched into two sections. The two emission ends 151b and 151c are detachably connected to the microscope body 4. The emission end 151b is connected to the illuminating optical passage 129 for the microscope of the microscope body 4 similarly to the ninth embodiment. That is, the converging lens 126, the illuminating zoom lens 127, the illuminating prism 128 and the objective lens 120 of the illuminating optical passage 129 for the microscope are sequentially disposed from the emission end 151b. That is, the illuminating-light branching means according to this embodiment is constituted by the divided light guide fiber.

The other emission end 151c is connected to a connecting portion 152 projecting over the lower portion of the microscope body 4. The connector 106g of the light guide cable 106d of the endoscope 106 is detachably connected to the connecting portion 152. In the connecting portion 152, the emission end 151d of the light guide fiber 151 is disposed directly opposite to the incident end 106f of the light guide fiber 106e in the light guide cable 106d so as be brought into contact with the incident end 106f.

(Operation)

Light emitted from the light source unit 5 is split by the light guide fiber 151 so as to be introduced into the illuminating optical passage 129 for the microscope and the light guide fiber 106e of the endoscope 106, respectively. Thus, the portion which must be observed with the microscope and the portion which must be observed with the endoscope are simultaneously illuminated.

The illuminating optical passage 129 for the microscope according to this embodiment has a usual structure. Moreover, splitting of light to the endoscope 106 is performed by only the light guide fiber 151. Therefore, the structure of the microscope body 4 can considerably be simplified and size reduction is permitted.

[Twelfth Embodiment]

Figure 18:
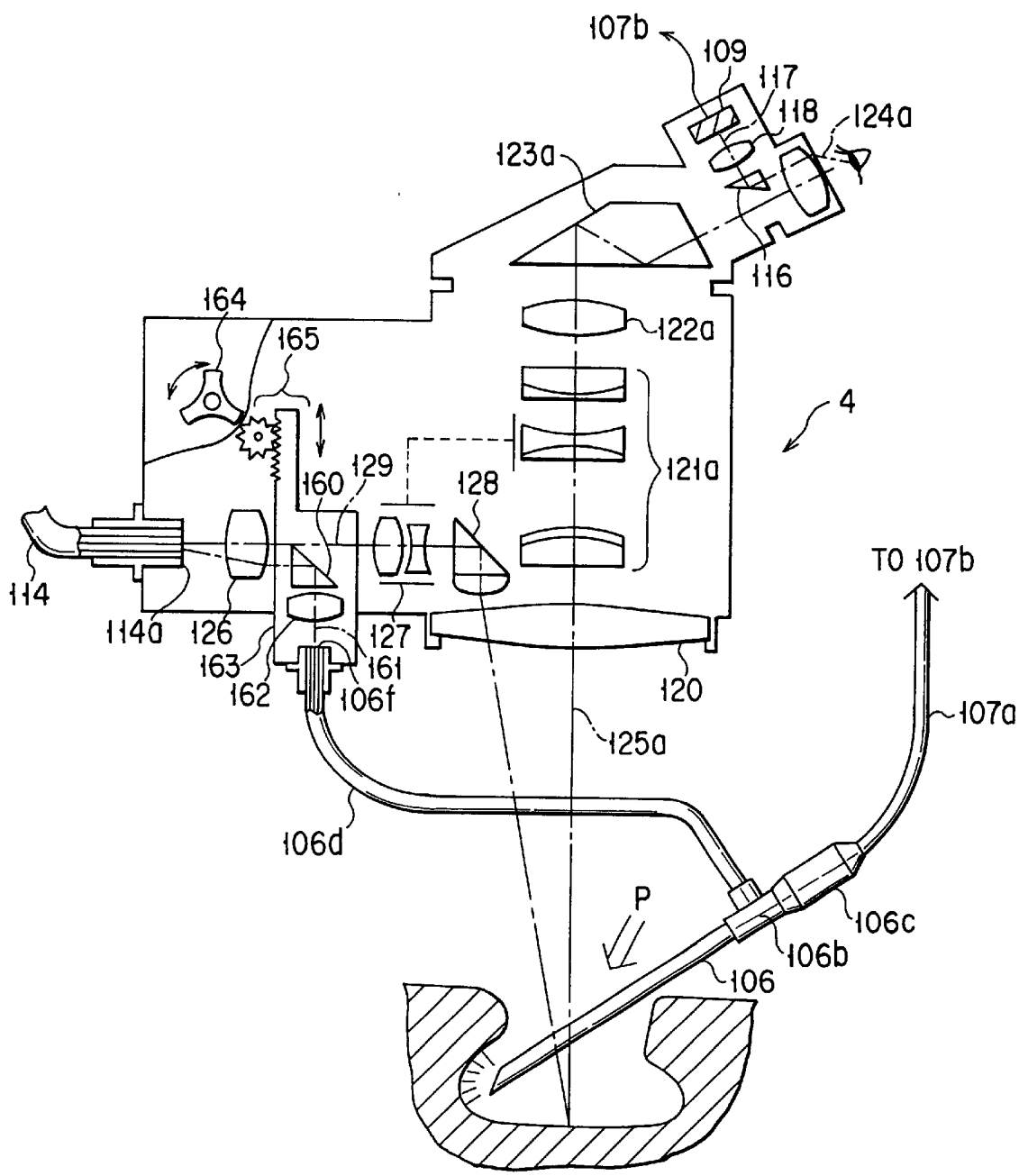
FIG. 18 is a diagram schematically showing the structure of a surgical microscope apparatus according to a twelfth embodiment.

Referring to FIG. 18, a twelfth embodiment of the present invention will now be described.

This embodiment is different from the ninth embodiment in only the structure of the illuminating optical passage 129 for the microscope and the endoscope illuminating optical passage 131.

FIG. 18 shows the structures of the microscope body 4 and its peripheral equipment. Referring to FIG. 18, reference numeral 160 represents a prism disposed in the illuminating optical passage 129 for the microscope and arranged to serve as the means for optically splitting the optical passage. The prism 160 deflects a portion of light allowed to pass through the illuminating optical passage 129 for the microscope to form a new endoscope illuminating optical passage 161.

Similarly to the ninth embodiment, a converging lens 162, and the incident end 106f of the light guide cable 106d for the endoscope are disposed in the endoscope illuminating optical passage 161. The prism 160, the converging lens 162 and the incident end 106f of the light guide cable 106d for the endoscope are integrally provided for a housing 163. The housing 163 can be moved in the axial direction of the endoscope illuminating optical passage 161 with respect to the microscope body 4 by a gear transmission mechanism 165 incorporating a rack and pinion when a dial 164 is rotated. That is, a light-quantity varying means is constituted which is capable of varying the length of the prism 160 which is inserted into the microscope illuminating optical passage 29. Moreover, the quantity of light which is branched to the endoscope illuminating optical passage 161 can be varied.

(Operation)

Light emitted from the light emission end 114a allowed to pass through the illuminating optical passage 129 for the microscope is partially split by the prism 160. Then, light is introduced into the light guide cable 106d of the light guide fiber 6 through the converging lens 162. Thus, the portion P to be operated, that is, the portion which must be observed with the endoscope 106, is illuminated from the distal end of the endoscope 106.

When light for the endoscope 106 is brightened during the operation, the quantity of light which is split from the illuminating optical passage 129 for the microscope to the endoscope illuminating optical passage 161 is enlarged by rotating the dial 164. Thus, the housing 163 is slid through the gear transmission mechanism 165 so as to widely insert the prism 160 into the illuminating optical passage 129 for the microscope. Thus, the quantity of split light is enlarged.

As a matter of course, when only the surgical microscope apparatus 1 is used and the endoscope 106 is not used, the prism 160 is removed from the illuminating optical passage 129 for the microscope. Thus, intense light can be supplied to the surgical microscope.

In this embodiment, the proportion of the light for the microscope and that for the endoscope can be varied. Therefore, the operation can be performed with optimum light.

[Thirteenth Embodiment]

Figure 19:
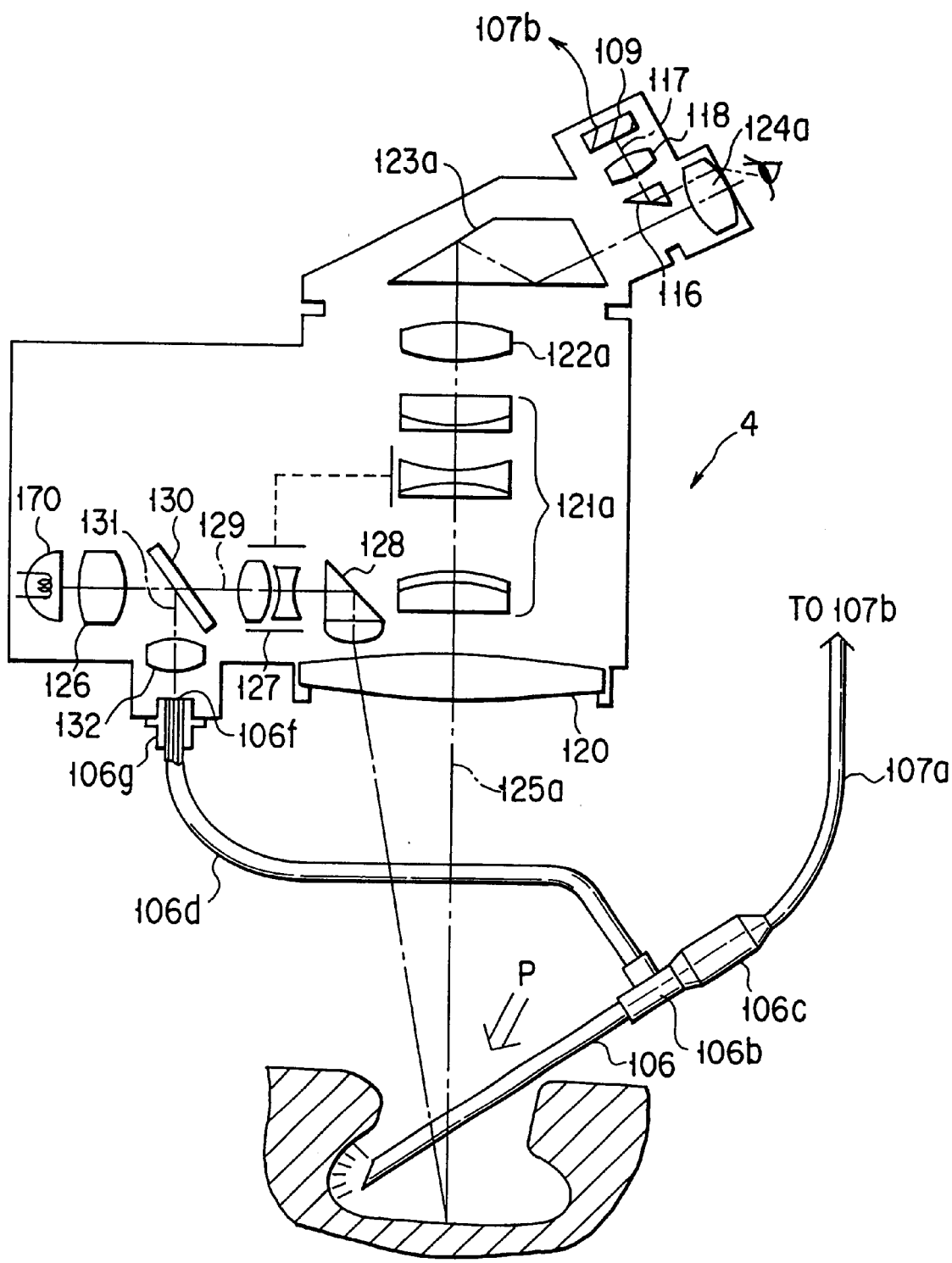
FIG. 19 is a diagram schematically showing the structure of a surgical microscope apparatus according to a thirteenth embodiment.

Referring to FIG. 19, a thirteenth embodiment of the present invention will now be described.

This embodiment has a structure that the method of transmitting light from the light source unit according to the ninth to twelfth embodiments to the microscope body 4 through the light guide fiber is changed. Moreover, a lamp is directly accommodated in the microscope body 4. Description will be made about a state in which the ninth embodiment is modified. This embodiment is different from the ninth embodiment in that a lamp 170 having a reflecting mirror is provided for the illuminating optical passage 129 for the microscope as a substitute for the emission end of the light guide. The lamp 170 is operated to emit light by a power source (not shown) accommodated in the frame portion 2.

Light emitted from the lamp 170 is transmitted to the portion P to be operated due to similar action to that of the ninth embodiment.

Since the lamp 170 is directly accommodated in the microscope body 4, loss of light occurring passage through the light guide fiber can be reduced. Therefore, efficient illumination can be performed.

Then, the endoscope for use together with the surgical microscope apparatus 1 will now be described. The following endoscope has operability improved when observation with the microscope is performed.

A hard scope is inserted into the body cavity while observation with a surgical microscope is being performed. The hard scope permits observation of a portion having a predetermined angle which is made from the direction of insertion. The insertion direction of the hard scope is not limited. The direction of observation with the hard scope in a plane perpendicular to the insertion direction of the hard scope can easily be determined in the observation field of view for the surgical microscope.

Figure 20:
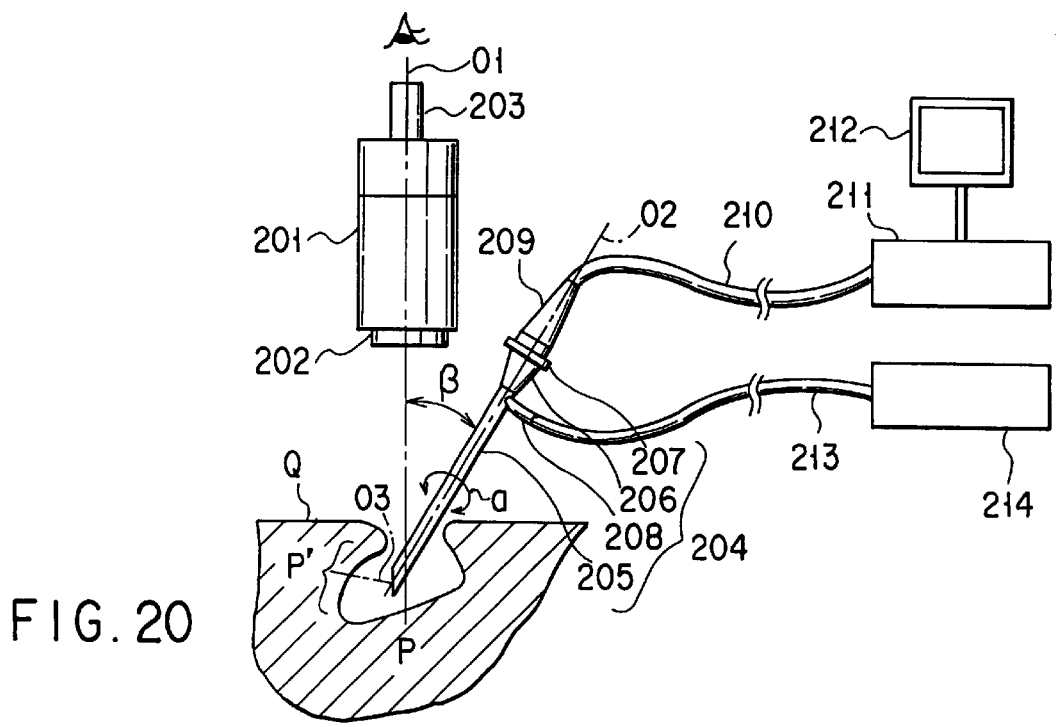
FIG. 20 is a diagram showing a connecting system of a hard scope according to a fourteenth embodiment and arranged to be used together with the surgical microscope apparatus according to the present invention.
Figure 21:
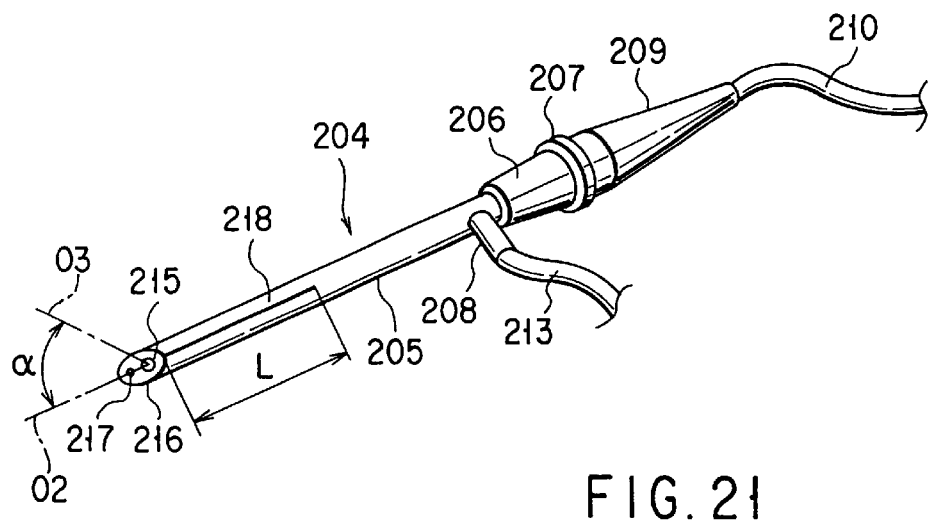
FIG. 21 is a perspective view showing the hard scope shown in FIG. 20.
Figure 22:
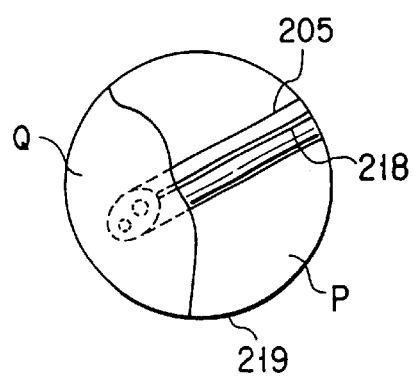
FIG. 22 shows an image of observed portion P which is operated in an observation field of view for the surgical microscope.
Figure 23A:
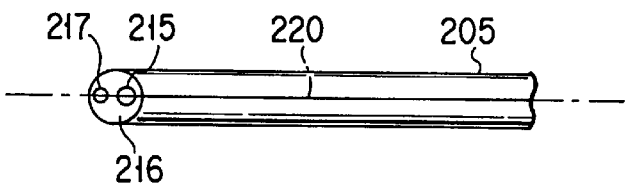
FIGS. 23A to 23C are a plan view, a front view and a bottom view, respectively, showing an insertion portion of a hard scope according to a fifteenth embodiment.
Figure 23B:
Figure 23C:
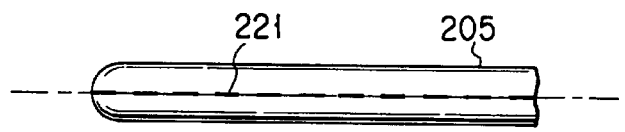

FIGS. 20 to 22 show a fourteenth embodiment of the endoscope.

Referring to FIG. 20, the overall structure of the system will now be described. A surgical microscope apparatus 201 is, by a frame arm (not shown), held and secured at a three-dimensional spatial position required for an operator. The surgical microscope apparatus 201 incorporates an objective-system housing 202 holding an objective optical system (not shown); a finder 203 holding an ocular optical system (not shown); and a magnitude varying optical system (not shown) for varying the observation magnitude. The objective optical system, the magnitude varying optical system and the ocular optical system are optically connected to one another. The operator is able to observe the portion P to be operated in a direction of optical axis $O_1$ of the objective optical system by the finder 203.

Reference numeral 204 represents a hard scope which is inserted into the portion P to be operated. The hard scope 204 incorporates an insertion portion 205, a handle portion 206, an ocular portion 207 and a metal light-guide joint 208. Reference numeral 209 represents a TV camera detachably joined to the ocular portion 207 of the hard scope 204 and arranged to photograph the image observed with the hard scope 204. The TV camera 209 is, by a cable 210, electrically connected to a control unit 211 which converts an obtained electric signal into an image signal. The control unit 211 is connected to a monitor 212 for displaying the image signal obtained by the hard scope 204. The metal light-guide joint 208 is connected to a light source unit 214 through a light guide 213.

Referring to FIG. 21, the structure of the hard scope 204 will now be described. Reference numeral 215 represents an objective lens disposed at the distal end 216 of the insertion portion 205 and having optical axis $O_3$. The optical axis $O_3$ of the objective lens 215 is disposed in the ocular portion 207 such that a predetermined angle α, which is, for example, 30°, 70° or 110°, is made from the optical axis $O_2$ of an ocular lens (not shown) which serves as the central axis in the insertion direction of the insertion portion 205. The optical axis $O_3$ of the objective lens and the optical axis $O_2$ of the ocular lens are optically connected to each other by a relay optical system (not shown) disposed in the insertion portion 205 and the handle portion 206. Moreover, an ocular lens (not shown) is disposed in the ocular portion 207. Thus, an observed image which is transmitted by the objective lens 215 and the relay optical system is formed on a light receiving device in the TV camera 209.

Reference numeral 217 represents an illuminating lens provided in the distal end 216 of the insertion portion 205 and arranged to emit light in substantially the same direction as that of the optical axis $O_3$ of the objective lens 215. The illuminating lens 217 is optically connected to a light guide 213 by the insertion portion 205 and an illuminating optical system (not shown) disposed in the metal light-guide joint 208. The light guide 213 is detachably connected to the metal light-guide joint 208.

Reference numeral 218 represents an identifying means, that is, a line, for indicating the direction of the optical axis $O_3$ of the objective lens 215 with respect to the optical axis $O_2$ of the ocular lens, that is, the direction of observation. The line 218 is stamped on the outer surface of the insertion portion 205 in a range for a predetermined distance L from the distal end 216 along a portion to which the optical axis $O_3$ of the objective lens 215 extends, that is the straight line in the vicinity of the observation portion of two straight line formed by intersecting one plane containing both of the optical axes $O_2$ and $O_3$ and the outer surface of the insertion portion 205 intersect. Also a second microscope (not shown) structured such that the outer diameter of the insertion portion 205 and the angle a between the optical axes $O_2$ and $O_3$ are different may have the same structure as that of the hard scope 204 except for the foregoing structure. When the TV camera 209 is removed from the ocular portion 207 of the first hard scope 204 and the light guide 213 is removed from the metal light-guide joint 208 so as to be joined to the ocular portion 207 and the metal light-guide joint 208 of the second hard scope, change from the first hard scope 204 is performed.

The operation of the endoscope according to the fourteenth embodiment will now be described.

The operator moves the surgical microscope apparatus 201 to a position above the portion P to be operated while adjusting the position and the angle of optical axis $O_1$ to a required position and angle. Light emitted from the portion P to be operated is allowed to pass through the objective optical system, the magnitude varying optical system and the ocular optical system of the surgical microscope apparatus 201, and then enlarged at a required magnification by the finder 203 so as to be observed by the operator. Then, observation of region P' (see FIG. 20) which is observed in an observation field of view 219 (see FIG. 22) for the surgical microscope apparatus 201, that is, the blind spot portion for the surgical microscope apparatus 201 is performed with the hard scope 204.

Initially, the operator holds the handle portion 206 of the hard scope 204 by the hand to move the hard scope 204 in the direction of the optical axis $O_3$ of the ocular lens of the hard scope 204 in a state where the operator looks the finder 203 of the surgical microscope apparatus 201. Thus, the operator inserts the distal end 216 of the insertion portion 205 into the portion P to be operated. Light which is supplied to the hard scope 204 from the light source unit 214 through the light guide 213 is guided to a position in the vicinity of the blind spot portion P' by the ocular optical system of the hard scope 204 and the illuminating lens 217. The operator rotates the hard scope 204 in a direction indicated with an arrow a around the optical axis $O_2$ of the ocular lens. Moreover, the operator adjusts angle β made from the optical axis $O_2$ of the ocular lens. Thus, adjustment is performed in such a manner that the optical axis $O_3$ of the objective lens 215 is brought to a required position of the blind spot portion P'. Thus, light emitted from the blind spot portion P' is transmitted to the ocular lens through the objective lens 215 of the hard scope 204 and the relay optical system (not shown). The ocular lens causes an image to be formed on an image pickup device of the TV camera 209 so as to be converted into an electric signal. The electric signal is converted into an image signal by the control unit 211, and then displayed on the monitor 212 as the image obtained by the hard scope 204 so as to be observed by the operator.

The image observed by the surgical microscope apparatus 201, that is, the image obtained by observing the portion P to be operated, as shown in FIG. 22, contains a portion of the insertion portion 205 of the hard scope 204. Therefore, also the line index 218 stamped on the outer surface of the insertion portion 205 of the hard scope 204 is, together with the image of the portion P to be operated, observed with the finder 203 of the surgical microscope apparatus 1. Therefore, the operator is able to identify the direction in a plane perpendicular to the optical axis $O_3$ of the objective lens 215 of the hard scope 204, that is, the direction in which the hard scope 204 has been inserted for the observation.

When the operation for adjusting the optical axis $O_3$ of the hard scope 204 to the blind spot portion P' for the surgical microscope apparatus 201 is difficult, the operator selects a second hard scope having the structure that the angle a of the optical axis $O_3$ and the outer diameter of the same are different. Then, the operator removes the TV camera 209 and the light guide 213 from the hard scope 204 and connects the same to the second hard scope. Thus, the operator again attempts observation of the blind spot portion P'.

In this embodiment, the identifying means for identifying a direction of observation of the objective lens in a plane perpendicular to the direction of insertion of the hard scope 204 is a simple structure that the line index 218 is stamped on the outer surface of the insertion portion 205 coinciding the direction of the optical axis $O_3$. The operator is able to easily recognize the direction of observation in the plane perpendicular to the insertion direction of the hard scope 204 in the observation field of view for the surgical microscope apparatus 201. Therefore, depriving of the orientation between the image observed with the surgical microscope apparatus 201 and that with the hard scope 204 can be prevented. When a variety of hard scopes having different angles between the optical axes $O_2$ and $O_3$ and the insertion portion 205, the outer diameter of which is different, are prepared and similar line index 218 is stamped on each hard scope, a hard scope can selectively be used to be adaptable to the state of the portion to be operated. Therefore, the operator is always able to maintain the optimum state of observation.

In this embodiment of the endoscope, the length of the line index 218 is made to be L which is a range of the insertion portion 205 which can be observed in the observation field of view 219 for the surgical microscope apparatus 201. As a matter of course, a similar effect can be obtained when the line index is provided for the overall portion of the insertion portion 205.

In this embodiment of the endoscope, the image observed with the hard scope 204 is displayed on the monitor 212. The structure disclosed in U.S. Pat. No. 5,601,549 which is cited in this specification may be employed such that the image of the hard scope is displayed in the observation field of view for the microscope. In the foregoing case, a similar effect can be obtained. Moreover, when an operator observes an image obtained by the hard scope, a necessity of release the sight of the finder 203 of the surgical microscope apparatus 201 can be eliminated. As a matter of course, the efficiency of the operation can furthermore be improved.

In this embodiment of the endoscope, the hard scope 204 is fixed by the operator who holds the handle portion 206 by the hand. As an alternative to the hand of the operator, a hard scope holder may be employed to fix the hard scope to the surgical microscope apparatus 201 or the operation bed.

FIGS. 23A, 23B, 23C, 24A and 24B show a fifteenth embodiment of the endoscope.

Reference numerals 220 and 221 represent an identifying means for identifying a direction in which observation with the hard scope 204 is performed. Reference numeral 220 represents a solid-line index stamped on a straight line on which a plane containing both of the optical axis $O_2$ of the ocular lens and the optical axis $O_3$ of the objective lens 215 and the outer surface of the insertion portion 205 in a portion to which the optical axis $O_3$ extends intersect. On the other hand, reference numeral 221 represents a solid-line index stamped on the outer surface of the hard scope 204 at a position opposite to the solid-line index 220 by an angular degree of about 180°.

The operation of the fifteenth embodiment of the endoscope will now be described.

Figure 24A:
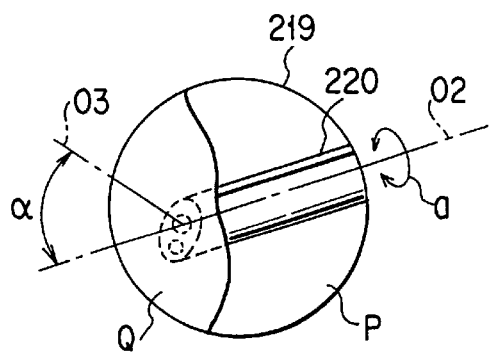
FIGS. 24A and 24B are diagrams each showing a state where an observed image in an observation field of view for the surgical microscope is obtained by rotating the hard scope around the optical axis of an ocular lens by about 180°.
Figure 24B:
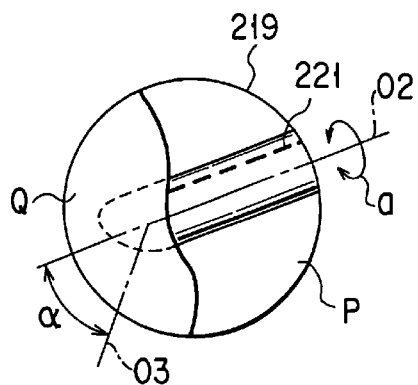
Figure 25A:
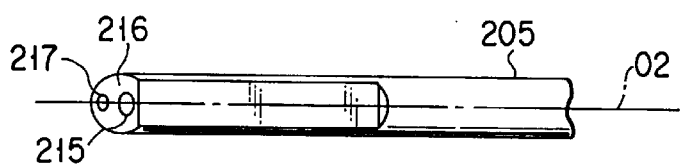
FIGS. 25A and 25B are a plan view and a side view, respectively, showing an insertion portion of a hard scope according to a sixteenth embodiment.
Figure 25B:
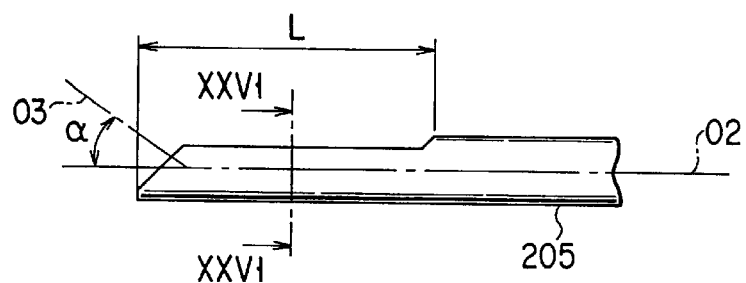

When the operator observes the blind spot portion P' for the surgical microscope apparatus 201, the operator selects a hard scope similarly to the fourteenth embodiment of the endoscope. Then, the operator moves the hard scope 204 in the direction of the optical axis $O_2$ of the ocular lens to insert the distal end 216 into the portion P to be operated. The foregoing state is shown in FIG. 24A. The solid-line index 221 stamped on the outer surface of the insertion portion 205 of the hard scope 204 is observed together with the image of the portion P to be operated in the observation field of view of the surgical microscope apparatus 201. The direction of the optical axis $O_3$ of the objective lens 215 of the hard scope 204 can be recognized. Then, the operator rotates the hard scope 204 in the direction indicated with an arrow a around the optical axis $O_2$ of the ocular lens or adjusts the angle β from the optical axis $O_1$ of the surgical microscope apparatus 201 similarly to the fourteenth embodiment. Thus, the operator adjusts the optical axis $O_3$ of the objective lens 215 of the hard scope 204 to a required portion of the blind spot portion P'. The foregoing state is shown in FIG. 24B. As the operator rotates the hard scope 204 around the optical axis $O_2$ of the ocular lens, the optical axis $O_3$ of the objective lens of the hard scope 204 sometimes faces the direction of the optical axis $O_1$ of the surgical microscope apparatus 201, that is, a downward portion of the drawing sheet on which FIGS. 24A and 24B are drawn. At this time, the dashed-line index 222 stamped on the outer surface of the insertion portion 205 of the hard scope 204 is observed simultaneously with the image of the portion P to be operated in the observation field of view 219 of the surgical microscope apparatus 201. Thus, the direction of the optical axis $O_3$ of the objective lens 215 of the hard scope 204 can be recognized by the operator.

In this embodiment, when the hard scope 204 is rotated around the optical axis $O_2$ of the ocular lens to shift the portion which is observed with the hard scope 204, the dashed-line index 222 for identifying the state of the hard scope 204 is stamped on the outer surface of the hard scope 204 causes the following effect. That is, the operator is able to easily recognize the direction of observation in the plane perpendicular to the direction of insertion of the hard scope 204 in the observation field of view 219 of the surgical microscope apparatus 201 regardless of the situation. Therefore, depriving of the orientation of between the image observed with the surgical microscope apparatus 201 and the image observed with the hard scope 204 can be prevented.

In this embodiment, the solid-line index 221 serves as the means for identifying the direction of observation with the objective lens in the plane with respect to the direction of insertion of the hard scope 204. Moreover, the dashed-line index 222 serves as the identifying means for the opposite portion. Any indexes may be employed to obtain a similar effect if the two indexes have different shapes. For example, the relationship of display realized by the solid-line index 221 and the dashed-line index 222 may be reversed. The indexes may be double lines, alternate long and short dash lines or alternate long and two short dashes lines.

In this embodiment, the identifying means is constituted by two indexes formed on the outer surface of the hard scope 204. Three or more stamps may be employed to obtain a similar effect if the correlation can be obtained with respect to the objective lens 215 of the hard scope 204. For example, it might be considered feasible to employ a method with which different indexes are stamped at three or four different positions obtained by dividing the outer surface of the insertion portion 205 into three or four sections about the position of the objective lens 215.

FIGS. 25A, 25B, 26 and 27 show a sixteenth embodiment of the endoscope.

Reference numeral 225 represents a shape deformed portion serving as a means for identifying the direction of observation with the hard scope 204 according to this embodiment and formed in a range having predetermined length L from the distal end 216 of the insertion portion 205 of the hard scope 204. A plane perpendicular to a plane including the optical axis $O_2$ of the ocular lens and the optical axis $O_3$ of the objective lens 215 is formed in the portion in the vicinity of the optical axis $O_3$ of the objective lens 215 of the hard scope 204. As shown in FIG. 26, the cross sectional shape is formed into a D-shape having width E with respect to the outer size D of the insertion portion 205 of the hard scope 204.

The operation of the sixteenth embodiment of the endoscope will now be described.

Similarly to the operation for the endoscope according to the fourteenth and fifteenth embodiments, the operator observes the blind spot portion P' for the surgical microscope apparatus 201. The operator selects a hard scope for use, and then the operator moves the hard scope 204 to the direction of the optical axis $O_2$ of the ocular lens to insert the distal end 216 into the portion P to be operated. Then, the operator rotates the hard scope 204 in the direction indicated with the arrow about the optical axis $O_2$ of the ocular lens and adjusts the angle b from the optical axis $O_1$ of the surgical microscope apparatus 201 to move the optical axis $O_3$ of the objective lens 215 of the hard scope 204 to a required portion in the blind spot portion P'. At this time, the portion P to be operated and the shape deformed portion 225 of the insertion portion 205 of the hard scope 204 can simultaneously be obtained in the observation field of view 219 of the surgical microscope apparatus 201 as shown in FIG. 27. Thus, the direction of the optical axis $O_3$ of the objective lens 215 which is the direction of observation performed with the hard scope 204 can be recognized by the operator.

In this embodiment, the identifying means for identifying the direction of observation with the objective lens in the plane perpendicular to the insertion direction of the hard scope 204 is the shape deformed portion 225. The shape deformed portion 225 has a cross sectional shape which is asymmetrical with respect to the optical axis $O_2$ of the ocular lens at the correlation position with the objective lens 215 in the insertion portion 205 of the hard scope 204. If blood or humoris of the portion to be operated adheres to the outer surface of the hard scope 204 during the operation, the shape deformed portion 225 can be identified. That is, a complicated operation is not required with which the hard scope 204 is temporarily removed from the portion to be operated to wipe out the accretion. Thus, the direction of observation with the hard scope 204 in the plane perpendicular to the insertion direction can easily be recognized. Therefore, depriving of the orientation between the image observed with the surgical microscope apparatus 201 and that observed with the hard scope 204 can be prevented.

In this embodiment, the shape deformed portion 225 has the D-shape cross sectional shape. As a matter of course, a similar effect can be obtained from a structure that a portion of the circular cross sectional shape of the insertion portion 205 is deformed, that is, a V-shape groove or a circularly spot-faced portion.

FIGS. 28 to 31 show a seventeenth embodiment of the endoscope.

Referring to FIGS. 28 and 29, the overall structure will now be described. Reference numeral 230 represents a sheath having a hard scope channel 231 and a treatment channel 232. Reference numeral 233 represents a holder connected to an operation bed 234. Either one of the holders 233 can be connected to a handle 235 of the sheath 230. The sheath 230 can reliably be held and secured by the holder 233. Reference numeral 236 represents a known treatment tool which can be inserted into the treatment channel 232 of the sheath 230. When the handle 237 is moved in a direction indicated with an arrow 238, biopsy of the portion P to be operated can be performed by a pair of forceps 239 disposed at the distal end.

Referring to FIG. 30, the structure of the hard scope 204 will now be described. Reference numeral 240 represents a laser diode which is a projecting means for emitting substantially circular index. The laser diode 240 is provided for a laser housing 241 joined integrally with the handle portion 206 in such a manner that the projection optical axis $O_4$ of the laser diode 240 is contained in a plane containing the optical axis $O_2$ of the ocular lens of the hard scope 204 and the optical axis $O_3$ of the objective lens 215.

The laser housing 241 accommodates a power source (not shown) and a drive circuit (not shown) for causing the laser diode 240 to emit light. Reference numeral 242 represents a switch joined to the outer surface of the laser housing 241, the switch 242 being electrically connected to output an input signal to the drive circuit.

The operation of the seventeenth embodiment of the endoscope will now be described.

Similarly to the fourteenth, fifteenth and sixteenth embodiments of the endoscope, the operator observes the blind spot portion P' for the surgical microscope apparatus 201. The operator moves the sheath 230 to a position in the vicinity of the blind spot portion P' for the surgical microscope apparatus 201. Then, the operator uses the holder 233 to reliably hold and secure the sheath 230. Then, the hard scope 204 is inserted into the hard scope channel 231 of the sheath 230 to straight move the hard scope 204 to the direction of the optical axis $O_2$ of the ocular lens. Thus, the distal end 216 of the hard scope 204 is inserted into the portion P to be operated. In the foregoing state, the switch 242 provided for the laser housing 241 is depressed to turn the laser diode 240 on. The laser diode 240 emits the projection index into the direction of the projection optical axis $O_4$. Thus, index R is projected to the intersection between the portion P to be operated and the projection optical axis $O_4$.

Then, the operator adjusts the optical axis $O_3$ of the objective lens 215 of the hard scope 204 to a required portion in the blind spot portion P' by rotating the hard scope 204 about the optical axis $O_2$ of the ocular lens in the direction indicated with the arrow a in the hard scope channel 231 of the sheath 230. To correspond to the foregoing adjustment operation, the projected index R is rotated in the directions indicated with arrows b and b' in the observation field of view 219 for the surgical microscope apparatus 201. Since the optical axes $O_2$, $O_3$ and $O_4$ exist in the same plane as described above, the optical axis $O_3$ of the objective lens 215 always exist on the extension line in the direction of the projection optical axis $O_4$ of the index R. Therefore, the direction of the optical axis $O_3$ of the objective lens 215 in the plane perpendicular to the insertion direction, which is the direction of observation which is performed with the hard scope 204, can be recognized by the operator in accordance with the position of the index R on the portion P to be operated.

When the biopsy or the like of the blind spot portion P' is performed while observation with the hard scope 204 is being performed, the operator inserts the treatment tool 236 into the treatment channel 232 of the sheath 230 to straight move the treatment tool 236 in the direction of the optical axis $O_2$. Thus, the forceps 239 of the treatment tool 236 is moved to a position in the vicinity of the blind spot portion P'. When the handle 237 of the treatment tool 236 is operated in the direction indicated with an arrow 238, the blind spot portion P' can be treated.

In this embodiment, the identifying means for identifying the direction of observation with the objective lens in the plane with respect to the insertion direction of the hard scope 204 is the laser diode 240 provided for the handle portion 206 of the hard scope 204. The index R is caused to emit light by the laser diode 240 so as to be projected to the portion P to be operated. When the blind spot portion P' is treated by using the hard scope 204 through the hard scope channel 231 of the sheath 230, the identifying means for identifying the observation direction with the hard scope 204 can always be recognized. Thus, the direction of observation with the hard scope 204 in the plane perpendicular to the insertion direction can easily be recognized. Therefore, depriving of the orientation between the image observed with the surgical microscope apparatus 201 and that observed with the hard scope 204 can be prevented.

Figure 34:
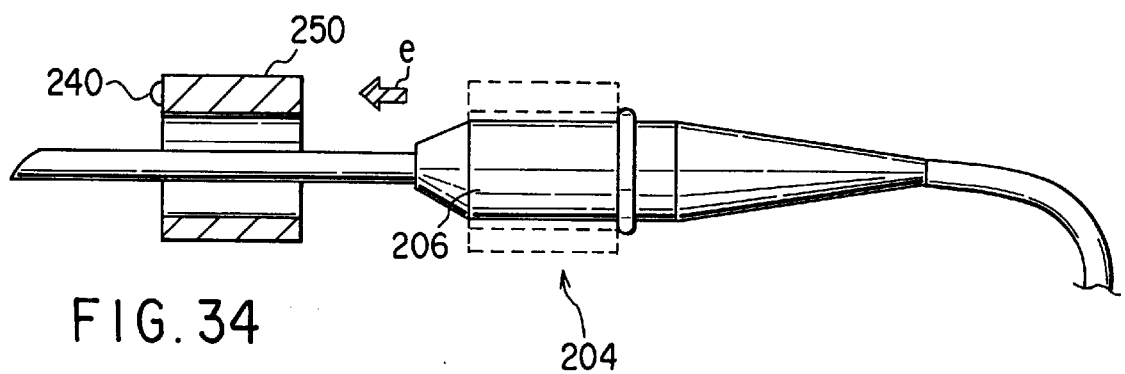
FIG. 34 is a diagram showing a method of joining an index projecting unit which can be joined to the hard scope to the hard scope.

FIGS. 32 to 34 show an eighteenth embodiment of the endoscope.

Referring to FIGS. 32 and 33, the structure of the hard scope 204 will now be described. Reference numeral 250 represents an index projecting unit accommodating the laser diode 240, a power source and a drive circuit for causing the laser diode 240 to emit light and the switch 242 for outputting an input signal to the drive circuit. Reference numeral 251 represents a fixed dial of the index projecting unit 250 having a structure that a thread portion 253 formed on the outer surface of a shaft 252 and a thread portion 254 of the index projecting unit 250 are engaged to each other. A securing member 255 is joined integrally to the distal end of the shaft 252.

The operation of the eighteenth embodiment of the endoscope will now be described.

When the operator observes the blind spot portion P' for the surgical microscope apparatus 201, the operator selects the outer size of the insertion portion 205 of the hard scope 204 and above-mentioned angle a according to the size of cut portion and a required observation direction. Then, the selected hard scope is inserted into the index projecting unit 250 in a direction indicated with an arrow e. Thus, the index projecting unit 250 is disposed at the position (a position indicated with a dashed line shown in FIG. 34) of the handle portion 206 of the hard scope 204.

Then, the index projecting unit 250 is rotated in a direction indicated with an arrow c shown in FIG. 32 to perform adjustment in such a manner that the projection optical axis $O_4$ of the laser diode 240 joined to the index projecting unit 250 is moved in the plane containing the optical axis $O_2$ of the ocular lens of the hard scope 204 and the optical axis $O_3$ of the monitor 212. Then, the fixed dial 251 is rotated in a direction indicted with an arrow d. Thus, the securing member 255 joined to the distal end of the shaft 252 of the fixed dial 251 is, by the thread portions 253 and 254, pressed against the handle portion 206 of the hard scope 204. Hence it follows that the index projecting unit 250 is secured to the handle portion 206 of the hard scope 204.

Similarly to the fourteenth to seventeenth embodiments of the endoscope, the operator moves the distal end of the hard scope 204 to the blind spot portion P' for the surgical microscope apparatus 201. Then, the operator operates the switch 242 to project the index R on the portion P to be operated by the laser diode 240. In the foregoing state, the hard scope 204 is rotated in the direction indicated with the arrow a around the optical axis $O_2$ of the ocular lens. Thus, the optical axis $O_3$ of the objective lens 215 is moved to a required position in the blind spot portion P'. Moreover, the position of the index R in the observation field of view 219 for the surgical microscope apparatus 201 enables the observation direction in the plane perpendicular to the insertion direction of the hard scope 204 to be recognized.

When the observation angle a with the hard scope 204 or the outer diameter of the insertion portion 205 is changed during the operation according to the state of the portion to be operated, the operator removes the hard scope 204 from the portion P to be operated. Then, the operator rotates the fixed dial 251 of the index projecting unit 250 in a direction opposite to the direction indicated with the arrow d to loosen the fixed dial 251. Then, the hard scope 204 is removed in a direction opposite to the direction indicated with an arrow e. Then, the index projecting unit 250 is joined to the employed hard scope by a method similar to the foregoing method. Then, the employed hard scope is moved to the inside portion of the portion P to be operated.

In this embodiment, the index projecting unit 250 for securing the laser diode 240 which emits the projection index is individually provided from the hard scope 204. Moreover, the index projecting unit 250 is made to be detachable with respect to the handle portion 206 of the hard scope 204. Therefore, any special hard scope is not required. When the index projecting unit 250 is joined to the conventional hard scope, the direction of observation in the plane perpendicular to the insertion direction of the hard scope 204 can easily be recognized regardless of the type of the hard scope. Therefore, depriving of the orientation between the image observed with the surgical microscope apparatus 201 and that observed with the hard scope 204 can be prevented.

Figure 35:
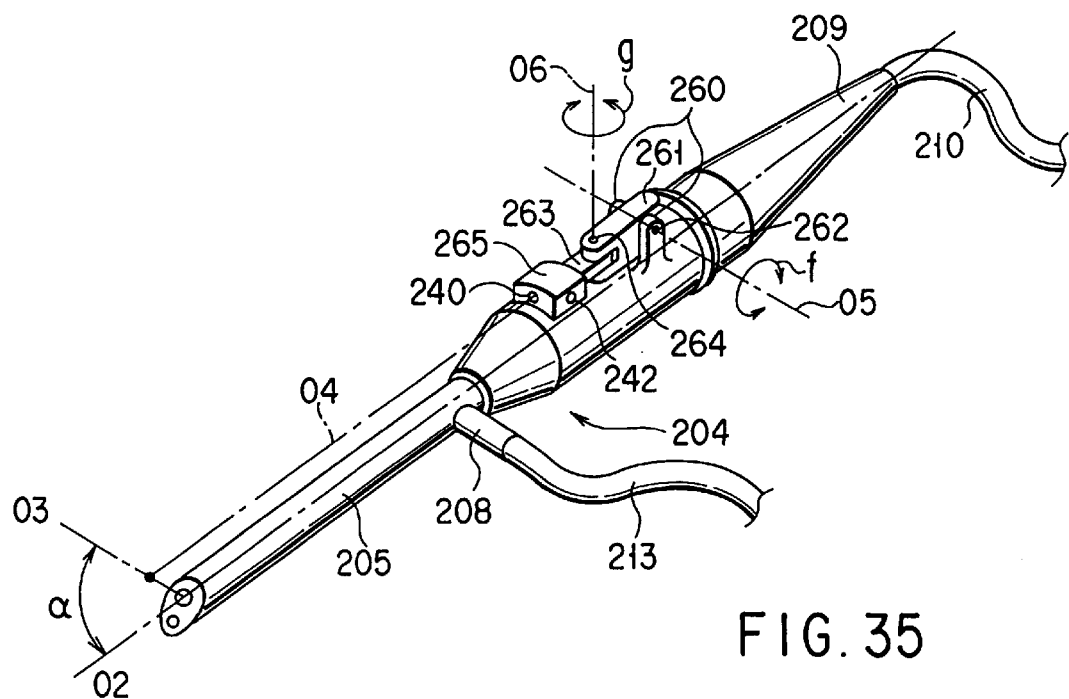
FIG. 35 is a perspective view showing a hard scope according to a nineteenth embodiment.
Figure 36:
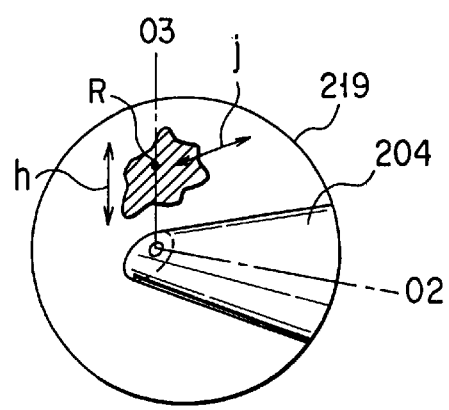
FIG. 36 shows an image observed with the hard scope shown in FIG. 35 in an observation field of view of the microscope.

FIGS. 35 and 36 show a nineteenth embodiment of the endoscope.

Referring to FIG. 35, the structure of the hard scope 204 will now be described. Reference numeral 260 represents a bearing portion joined integrally with the handle portion 206 of the hard scope 204. The bearing portion 260 rotatably and movably holds a first arm 261 in a direction indicated with an arrow f around a rotational central axis $O_5$ through a rotational shaft 262. Reference numeral 265 represents an index projection unit accommodating a laser diode 240, a power source and a drive circuit for causing the laser diode 240 to emit light and a switch 242 for outputting an input signal to the drive circuit. The index projecting unit 265 is integrally schematic to the second arm 263.

The operation of the nineteenth embodiment of the endoscope will now be described.

When the operator observes the blind spot portion P' for the surgical microscope apparatus 201 with the hard scope 204, the operator inserts the distal end 216 of the hard scope 204 into the portion P to be operated similarly to the fourteenth to eighteenth embodiments of the endoscope. The switch 242 of the index projecting unit 265 is operated to turn the laser diode 240 on. Thus, the index R is projected to the portion P to be operated. In the foregoing state, the hard scope 204 is rotated around the optical axis $O_2$ of the ocular lens so that the optical axis $O_3$ of the objective lens 215 is moved to a required position in the blind spot portion P'. Moreover, the observation direction in the plane perpendicular to the insertion direction of the hard scope 204 can be recognized according to the position of the index R in the observation field of view 219.

Blood and/or humoris exist in the portion to be operated and physiological saline is sometimes frequently sprinkled on the portion to be operated in order to clean the portion. The foregoing fluid frequently causes irregular reflection of light in the portion to be operated to occur. Therefore, when the index R which is projected to the portion P to be operated by the laser diode 240 is projected to the foregoing fluid, the identification is sometimes made to be impossible. In the foregoing case, the operator moves the first arm 261 for holding the index projecting unit 265 into a direction indicated with the arrow f by the rotational shaft 262 of the bearing portion 260 joined to the handle portion 206 of the hard scope 204. Moreover, the second arm 263 for holding the index projecting unit 265 is rotated in the direction indicated with an arrow g by the rotational shaft 264 connected to the first arm 261. Thus, the projection position of the index R is finely adjusted in a direction indicated with an arrow j in the observation field of view 219. Thus, recognition of the index R is permitted in the observation field of view 219.

This embodiment of the endoscope enables an operator to finely adjust the projection position of the index R, which is the identifying means for identifying the observation direction in the plane perpendicular to the insertion direction of the hard scope 204, on the portion to be operated according to the state of the portion to be operated. Therefore, recognition of the index R is satisfactorily permitted even if matter, such as blood, humoris or physiological saline, which irregularly reflects light exists in the portion to be operated.

Therefore, the observation direction in the plane perpendicular to the insertion direction of the hard scope 204 can easily be recognized regardless of the state of the portion to be operated. As a result, depriving of the orientation between the image observed with the surgical microscope apparatus 201 and that observed with the hard scope 204 can be prevented.

Although the invention has been described in its preferred form and structure with a certain degree of particularity, it is understood that the present disclosure of the preferred form can be changed in the details of construction and in the combination and arrangement of parts.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical microscope apparatus including a frame portion, an arm portion supported by said frame portion having an end capable of moving three-dimensionally, and a microscope body having first observation means provided on the end of the arm portion for stereoscopically observing a portion to be operated on, said surgical microscope apparatus comprising:

second observation means for observing said portion to be operated on;

a control unit for processing information on an image obtained by said second observation means;

a connecting portion provided on the microscope body, to which the second observation means is connected; and transmitting means for connecting said connecting portion to said control unit and for transmitting information on the image obtained by the second observation means to the control unit, wherein the second observation means is connected to the control unit via the transmitting means, and the information on the image obtained by the second observation means is transmitted to the control unit and processed by the control unit.

2. A surgical microscope according to claim 1, wherein:

the second observation means includes an endoscope having an image guide fiber, said endoscope having an objective lens which forms a portion of the image to be operated on for transmitting said image via the image guide fiber, said transmitting means has an entrance face for receiving the image of the portion to be operated on, which is transmitted via the image guide fiber, and has an image pickup head for forming an image signal on the basis of the image received via the entrance face, said entrance face opposes the image guide fiber of the endoscope when the endoscope is connected to the connecting portion, and has a cable for connecting the image pickup head to the control unit, and said control unit processes the image signal formed by the image pickup head and thereby forms an optical image.

3. A surgical microscope apparatus according to claim 2, further comprising:

a light source unit; and light guide means for guiding light from the light source unit to the connecting portion, and wherein said endoscope has an illuminating system connecting portion for connecting the light guide means to a light guide fiber included in the endoscope, and illuminates the portion to be operated on when connected to the light guide means via the illuminating system connecting portion.

4. A surgical microscope apparatus according to claim 3, further comprising displacement means capable of changing a position of the connecting portion with respect to the microscope body.

5. A surgical microscope apparatus according to claim 4, wherein:

said connecting portion has a plate-like member having an opening which forms an observation system connecting portion, and an opening which forms a light system connecting portion, and said displacement means has a supporting unit which supports the connecting portion in such a manner that the connecting portion can be moved.

6. A surgical microscope apparatus according to claim 4, wherein the connecting portion comprises:

a cylindrical member extended outwardly from the microscope body and provided along an outer surface of the microscope body;

a relay optical system contained in said cylindrical member for transmitting the observed image from the endoscope to the image pickup head;

light-transmitting means contained in the cylindrical member for transmitting light from said light guide means to the endoscope;

an opening for deforming an observation light incidence portion; and an opening for deforming a light emission end, wherein said displacement means includes fixing means for fixing the cylindrical member at a position wherein the cylindrical member is selectively rotated with respect to the image pickup head.

7. A surgical microscope apparatus according to claim 6, wherein said relay optical system has a zoom mechanism which enlarges and reduces the observed image.

8. A surgical microscope apparatus according to claim 2, further comprising:

an ultrasonic probe selectively usable for ultrasonic observation, said ultrasonic probe having a main body, an insertion portion which is extended from said main body and contains an ultrasonic oscillator, and a probe cable which is extended from the main body for transmitting an ultrasonic signal to said insertion portion;

an ultrasonic probe connecting portion provided on said image pickup head for connecting said ultrasonic probe;

an ultrasonic drive unit connected to the main body via said probe cable; and an ultrasonic signal cable extended from said ultrasonic drive unit for observing a signal from the ultrasonic probe by is using a monitor, said probe cable being electronically connected to said ultrasonic signal cable when the ultrasonic probe is connected to said ultrasonic probe connecting portion.

9. A surgical microscope apparatus according to claim 8, wherein:

said ultrasonic oscillator is rotatable within the insertion portion; and the ultrasonic probe is operatively coupled to said ultrasonic drive unit when connected to the ultrasonic probe connecting portion, and has an ultrasonic transmission portion for driving the ultrasonic oscillator contained in said insertion portion.

10. A surgical microscope apparatus according to claim 9, further comprising a holding portion, which is provided on the microscope body and which detachably holds at least one of the endoscope and the ultrasonic probe, and wherein:

said holding portion has a base attached to the microscope body, and a holder which is detachably attached to said base for holding at least one of the endoscope and the ultrasonic probe, and a sterilizing drape, for covering the microscope body to maintain in a sterile state, is fixable between the base and the holder.

11. A surgical microscope apparatus according to claim 1, wherein:

said second observation means includes an endoscope, said endoscope has an objective optical system, a TV camera head for taking an image of the portion to be operated on formed by said objective optical system, and an endoscope signal cable extended from said TV camera head, and said transmitting means has a cable extended in an arm portion for electrically connecting the TV camera head to said control means through said endoscope signal cable.

12. A surgical microscope apparatus according to claim 11, further comprising:

a light-source unit for illuminating the portion to be operated on; and a light guide fiber for guiding light to a place at a distance from said light-source unit, and wherein said endoscope has a light guide cable connected to the light guide fiber and which illuminates the portion to be operated on when connected to the light guide fiber via the light guide cable.

13. A surgical microscope apparatus according to claim 11, further comprising:

an ultrasonic probe selectively usable for performing an ultrasonic observation, said ultrasonic probe having a main body, an insertion portion extended from said main body and containing an ultrasonic oscillator, and a probe cable for transmitting an ultrasonic signal to said insertion portion;

an ultrasonic probe connecting portion provided on said microscope body for connecting said ultrasonic probe;

an ultrasonic drive unit connected to the main body via said probe cable; and an ultrasonic signal cable extended from said ultrasonic drive unit for observing a signal from the ultrasonic signal probe by using a monitor, said probe cable being electrically connected to the ultrasonic signal when the ultrasonic probe is connected to the ultrasonic probe connecting portion.

14. A surgical microscope apparatus according to claim 13, wherein:

said ultrasonic oscillator is rotatable within the insertion portion; and the ultrasonic probe is operatively coupled to said ultrasonic drive unit when connected to the ultrasonic probe connecting portion, and has an ultrasonic transmission portion for driving the ultrasonic oscillator contained in the insertion portion.

15. A surgical microscope apparatus according to claim 14, further comprising a holding portion provided on said microscope body and which detachably holds at least one of the endoscope and the ultrasonic probe, and wherein:

said holding portion has a base attached to the microscope body and a holder which is detachably attached to said base for holding at least one of the endoscope and the ultrasonic probe, and said holding portion being capable of fixing a sterilizing drape, for covering the microscope body to maintain it in a sterile state, between the base and the holder.

16. A surgical microscope apparatus according to claim 1, wherein:

said second observation means includes an ultrasonic probe for performing an ultrasonic observation, said ultrasonic probe having a main body, an insertion portion extended from the main body and which contains an ultrasonic oscillator, and a probe cable extended from the main body for transmitting an ultrasonic signal to the insertion portion, said connecting portion includes an ultrasonic drive unit connected to the main body via said probe cable, said transmitting means includes an ultrasonic signal cable extended from said ultrasonic drive unit for observing a signal from the ultrasonic probe by using a monitor, and said probe cable is electrically connected to the ultrasonic signal cable when the ultrasonic probe is connected to the connecting portion.

17. A surgical microscope apparatus according to claim 16, wherein:

said ultrasonic oscillator is rotatable within the insertion portion; and the ultrasonic probe is operatively coupled to said ultrasonic drive unit when connected to the connecting portion, and has an ultrasonic transmission portion for driving the ultrasonic oscillator contained in the insertion portion.

18. A surgical microscope apparatus according to claim 17, further comprising a holding portion provided on said microscope body and which detachably holds said ultrasonic probe, and wherein:

said holding portion has a base attached to the microscope body and a holder which is detachably attached to said base for holding at least one of the ultrasonic probe and the holding portion, and a sterilizing drape, for covering the microscope body to maintain it in a sterile state, is fixable between the base and the holder.

19. A surgical microscope apparatus including a frame portion, an arm portion supported by said frame portion and having an end capable of moving three-dimensionally, and a microscope body having first observation means for stereoscopically observing a portion to be operated on, said surgical microscope apparatus comprising:

a light-source for emitting light for illuminating a portion to be operated on;

first light guiding means for guiding the light from the light-source to the portion to be operated on;

second observation means for observing the portion to be operated on; and second light guiding means for supplying the light to the second observation means, wherein the second light guiding means is optically diverged from the first light guiding means.

20. A surgical microscope apparatus comprising:

a frame portion placed on a floor;

a microscope body having a stereomicroscope optical system for stereoscopically observing a portion to be operated on, and an outer surface;

an arm portion supported by the frame portion and arranged to suspend the microscope body at a position away from the frame portion;

an endoscope for observing a blind spot of an observation field of view of the stereomicroscope optical system;

a light source unit arranged to emit light to illuminate a portion to be observed with the endoscope;

light supply means having an end which is optically connectable to the endoscope and which is capable of supplying light from the light source unit to the endoscope;

a control unit provided in the frame portion and arranged to process an observed image of an observed portion obtained by the endoscope;

transmitting means having an end for interfacing the endoscope with the control unit and which transmits an observed image obtained by the endoscope to the control unit; and a connecting portion of the endoscope provided at the outer surface of the microscope body and structured to have end to the light supply means and the transmitting means;

wherein the endoscope includes an elongated and hard insertion portion having an axial line and a distal end arranged to be inserted into the microscope body along the axial tine, an objective optical system disposed at the distal end of the insertion portion, the objective optical system having an optical axis extending to make a predetermined angle from the axial line, and identifying means for indicating a direction in which the optical axis of the objective optical system extends, wherein the identifying means is stereoscopically observable through the stereomicroscope optical system.

21. A surgical microscope apparatus according to claim 20, wherein the identifying means has at least one index provided on an outer surface of the distal end.

22. A surgical microscope apparatus according to claim 20, wherein the identifying means is provided on the distal end of the insertion portion of the endoscope, and includes a shape deformed portion by which the endoscope portion is provided with cross sections that are asymmetric with respect to the axial line, the shape deformed portion representing an axial direction of the objection optical system.

23. A surgical microscope apparatus according to claim 20, wherein the identifying means includes a projecting unit joined to the endoscope and arranged to project an index to at least one of the portion to be operated on and the endoscope.

24. A surgical microscope apparatus according to claim 23, wherein the projecting unit includes a laser diode.

25. A surgical microscope apparatus according to claim 20, wherein the identifying means is detachably joined to the endoscope.

* * * * *

UNITED STATES PATENT AND TRADEMARK OFFICE
CERTIFICATE OF CORRECTION

PATENT NO. : 6,398,721 B1
DATED : June 4, 2002
INVENTOR(S) : Motokazu Nakamura et al.

It is certified that error appears in the above-identified patent and that said Letters Patent is hereby corrected as shown below:

<u>Title page,</u>
Insert -- Item [30] Foreign Priority Application Data
        Feb. 19, 1999  (Japan)      11-041806
        Mar. 30, 1999  (Japan)      11-089399
        Jan. 27, 2000  (Japan)      2000-018865 --.

Signed and Sealed this

Nineteenth Day of August, 2003

JAMES E. ROGAN
*Director of the United States Patent and Trademark Office*